(12) United States Patent
Duan et al.

(10) Patent No.: US 12,414,966 B2
(45) Date of Patent: *Sep. 16, 2025

(54) METHOD OF TREATING DIABETES WITH FGF21 AND GLP1 DOUBLE GENE-MODIFIED CELL

(71) Applicant: Beijing Jiyuan Biological Technology Co., Ltd., Beijing (CN)

(72) Inventors: Haifeng Duan, Beijing (CN); Binghua Xue, Beijing (CN); Jing Xie, Beijing (CN); Zhenli Zhang, Beijing (CN)

(73) Assignee: BEIJING JIYUAN BIOLOGICAL TECHNOLOGY CO., LTD., Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/357,639

(22) Filed: Jul. 24, 2023

(65) Prior Publication Data

US 2024/0100100 A1    Mar. 28, 2024

Related U.S. Application Data

(63) Continuation of application No. 16/954,763, filed as application No. PCT/CN2018/081616 on Apr. 2, 2018, now Pat. No. 11,752,173.

(30) Foreign Application Priority Data

Dec. 19, 2017    (CN) .......................... 201711374615.0

(51) Int. Cl.
- *A61K 35/28* (2015.01)
- *A61P 3/10* (2006.01)
- *C07K 14/50* (2006.01)
- *C07K 14/605* (2006.01)
- *C12N 5/0775* (2010.01)

(52) U.S. Cl.
CPC ............... *A61K 35/28* (2013.01); *A61P 3/10* (2018.01); *C07K 14/50* (2013.01); *C07K 14/605* (2013.01); *C07K 2319/30* (2013.01); *C12N 5/0662* (2013.01); *C12N 5/0663* (2013.01); *C12N 5/0665* (2013.01)

(58) Field of Classification Search
CPC ........... A61K 35/28; A61P 3/10; C07K 14/50; C07K 14/605; C07K 2319/30
See application file for complete search history.

(56) References Cited

U.S. PATENT DOCUMENTS

| | | | |
|---|---|---|---|
| 5,712,396 A | 1/1998 | Magnin et al. | |
| 11,752,173 B2 | 9/2023 | Duan et al. | |
| 2010/0068289 A1 | 3/2010 | Geigle et al. | |
| 2011/0034373 A1 | 2/2011 | Coskun et al. | |

FOREIGN PATENT DOCUMENTS

| | | |
|---|---|---|
| CN | 101712722 A | 5/2010 |
| CN | 102802657 A | 11/2012 |
| CN | 104024273 A | 9/2014 |
| CN | 104250655 A | 12/2014 |
| CN | 101974090 B | 6/2015 |
| CN | 104736558 A | 6/2015 |
| CN | 104805058 A | 7/2015 |
| CN | 102143758 B | 11/2015 |
| CN | 103328502 B | 6/2016 |
| CN | 103945871 B | 4/2017 |
| CN | 107108710 A | 8/2017 |
| CN | 109929806 B | 5/2020 |
| CN | 111518770 A | 8/2020 |
| WO | WO-8706941 A1 | 11/1987 |
| WO | WO-9638144 A1 | 12/1996 |
| WO | WO-9712613 A1 | 4/1997 |
| WO | WO-9712615 A1 | 4/1997 |
| WO | WO-9819698 A1 | 5/1998 |
| WO | WO-9900353 A1 | 1/1999 |
| WO | WO-0001389 A1 | 1/2000 |
| WO | WO-0039077 A2 | 7/2000 |
| WO | WO-2005061712 A1 | 7/2005 |
| WO | WO-2006028595 A2 | 3/2006 |
| WO | WO-2006028714 A1 | 3/2006 |
| WO | WO-2006065582 A2 | 6/2006 |
| WO | WO-2008121563 A2 | 10/2008 |

(Continued)

OTHER PUBLICATIONS

Bhattacharya et al., "Impact of Genetic Variation on Three Dimensional Structure and Function of Proteins," PLoS One 12(3):e0171355:(1-22) (Mar. 15, 2017).

(Continued)

*Primary Examiner* — Zachary C Howard

(74) *Attorney, Agent, or Firm* — WILSON SONSINI GOODRICH & ROSATI

(57) ABSTRACT

Provided are a modified mesenchymal stem cell and culture supernatant thereof, and a pharmaceutical composition comprising said cell or culture supernatant thereof. The mesenchymal stem cell is capable of expressing: (1) a first protein, which is selected from FGF21 or a variant thereof, or a first fusion protein comprising the FGF21 or the variant thereof; and (2) a second protein, which is selected from GLP-1 or a variant thereof or a second fusion protein comprising the GLP-1 or the variant thereof. Also provided is the use of the modified mesenchymal stem cell and culture supernatant thereof, and the pharmaceutical composition comprising said cell or culture supernatant thereof in the treatment of metabolic diseases and in the preparation of a medicament for treating metabolic diseases.

19 Claims, 8 Drawing Sheets

Specification includes a Sequence Listing.

(56) References Cited

FOREIGN PATENT DOCUMENTS

| WO | WO-2010142665 A1 | 12/2010 |
| WO | WO-2011056713 A2 | 5/2011 |
| WO | WO-2014152795 A2 | 9/2014 |
| WO | WO-2019119673 A1 | 6/2019 |

OTHER PUBLICATIONS

Dostálová, et al. Fibroblast growth factor 21: a novel metabolic regulator with potential therapeutic properties in obesity/type 2 diabetes mellitus. Physiol Res. 2009;58(1):1-7.
Holliger et al., "Diabodies": Small Bivalent and Bispecific Antibody Fragments. PNAS USA 90:6444-6448 (Jul. 1993).
International search report with written opinion dated Sep. 26, 2018 for PCT/CN2018/081616.
Kharitonenkov, et al. FGF-21 as a novel metabolic regulator. J Clin Invest. Jun. 2005;115(6):1627-1635. doi: 10.1172/JCI23606. Epub May 2, 2005.
Nauck, et al. Glucagon-like peptide 1 (GLP-1) as a new therapeutic approach for type 2-diabetes. Exp Clin Endocrinol Diabetes. 1997;105(4):187-195. doi: 10.1055/s-0029-1211750.
Notice of Allowance dated Apr. 24, 2023 for U.S. Appl. No. 16/954,763.
Office action dated Oct. 13, 2022 for U.S. Appl. No. 16/954,763.
Omar, et al. Fibroblast growth factor 21 (FGF21) and glucagon-like peptide 1 contribute to diabetes resistance in glucagon receptor-deficient mice. Diabetes. Jan. 2014;63(1):101-110. doi: 10.2337/db13-0710. Epub Sep. 23, 2013.
Poljak, R.J. Production and structure of diabodies. Structure. Dec. 15, 1994;2(12):1121-1123. doi: 10.1016/s0969-2126(94)00113-8.
Tokuriki et al., Stability Effects of Mutations and Protein Evolvability. Current Opinion in Structural Biology 19:596-604 (Sep. 16, 2009).
Xue, et al. Mesenchymal stem cells modified by FGF21 and GLP1 ameliorate lipid metabolism while reducing blood glucose in type 2 diabetic mice. Stem Cell Res Ther. Feb. 15, 2021;12(1):133. doi: 10.1186/s13287-021-02205-z.

```
                                SEQUENCE LISTING

Sequence total quantity: 22
SEQ ID NO: 1             moltype = AA   length = 209
FEATURE                  Location/Qualifiers
REGION                   1..209
                         note = Wild-type FGF21 full-length sequence
source                   1..209
                         mol_type = protein
                         organism = synthetic construct
SEQUENCE: 1
MDSDETGFEH SGLWVSVLAG LLLGACQAHP IPDSSPLLQF GGQVRQRYLY TDDAQQTEAH    60
LEIREDGTVG GAADQSPESL LQLKALKPGV IQILGVKTSR FLCQRPDGAL YGSLHFDPEA   120
CSFRELLLED GYNVYQSEAH GLPLHLPGNK SPHRDPAPRG PARFLPLPGL PPALPEPPGI   180
LAPQPPDVGS SDPLSMVGPS QGRSPSYAS                                    209

SEQ ID NO: 2             moltype = AA   length = 205
FEATURE                  Location/Qualifiers
REGION                   1..205
                         note = FGF21v amino acid sequence
source                   1..205
                         mol_type = protein
                         organism = synthetic construct
SEQUENCE: 2
MDSDETGFEH SGLWVSVLAG LLLGACQADS SPLLQFGGQV RQRYLYTDDA QQTEAHLEIR    60
EDGTVGGAAD QSPESLLQLK ALKPGVIQIL GVKTSRFLCQ RPDGALYGSL HFDPEACSFR   120
ELLLEDGYNV YQSEAHGLPL HCPGNKSPHR DPAPRGPCRF LPLPGLPPAL PEPPGILAPQ   180
PPDVGSSDPL AMVGPSQGRS PSYAS                                        205

SEQ ID NO: 3             moltype = DNA   length = 615
FEATURE                  Location/Qualifiers
misc_feature             1..615
                         note = FGF21v nucleotide encoding sequence
source                   1..615
                         mol_type = other DNA
                         organism = synthetic construct
SEQUENCE: 3
atggactcgg acgagaccgg gttcgagcac tcaggactgt gggtttctgt gctggctggt    60
cttctgctgg gagcctgcca ggcagactcc agtcctctcc tgcaattcgg gggccaagtc   120
cggcagcggt acctctacac agatgatgcc cagcagacag aagcccacct ggagatcagg   180
gaggatggga cggtgggggg cgctgctgac cagagccccg aaagtctcct gcagctgaaa   240
gccttgaagc cgggagttat tcaaatcttg ggagtcaaga catccaggtt cctgtgccag   300
cggccagatg gggccctgta tggatcgctc cactttgagc ctgaggcctg cagcttccgg   360
gagctgcttc ttgaggacgg atacaatgtt taccagtccg aagcccacgg cctcccgctg   420
cactgcccag ggaacaagtc cccacaccgg gaccctgcac cccgaggacc atgccgcttc   480
ctgccactac caggcctgcc ccccgcactc ccggagccac ccggaatcct ggccccccag   540
cccccccgatg tgggctcctc ggaccctctg gccatggtgg gaccttccca gggccgaagc   600
cccagctacg cttcc                                                   615

SEQ ID NO: 4             moltype = AA   length = 31
FEATURE                  Location/Qualifiers
REGION                   1..31
                         note = Wild-type GLP-1(7-37)OH amino acid sequence
source                   1..31
                         mol_type = protein
                         organism = synthetic construct
SEQUENCE: 4
HAEGTFTSDV SSYLEGQAAK EFIAWLVKGR G                                   31

SEQ ID NO: 5             moltype = AA   length = 31
FEATURE                  Location/Qualifiers
REGION                   1..31
                         note = GLP-1v amino acid sequence
source                   1..31
                         mol_type = protein
                         organism = synthetic construct
SEQUENCE: 5
HGEGTFTSDV SSYLEEQAAK EFIAWLVKGG G                                   31

SEQ ID NO: 6             moltype = DNA   length = 93
FEATURE                  Location/Qualifiers
misc_feature             1..93
                         note = GLP-1v nucleotide encoding sequence
```

| source | 1..93 |  |
|---|---|---|
|  | mol_type = other DNA |  |
|  | organism = synthetic construct |  |

SEQUENCE: 6
```
catggcgaag ggacctttac cagtgatgta agttcttatt tggaagagca agctgccaag   60
gaattcattg cttggctggt gaaaggcggc gga                                93
```

| SEQ ID NO: 7 | moltype = AA  length = 228 |  |
|---|---|---|
| FEATURE | Location/Qualifiers |  |
| REGION | 1..228 |  |
|  | note = IgG4 Fc amino acid sequence |  |
| source | 1..228 |  |
|  | mol_type = protein |  |
|  | organism = synthetic construct |  |

SEQUENCE: 7
```
ESKYGPPCPP CPAPEAAGGP SVFLFPPKPK DTLMISRTPE VTCVVVDVSQ EDPEVQFNWY   60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLG              228
```

| SEQ ID NO: 8 | moltype = DNA  length = 687 |
|---|---|
| FEATURE | Location/Qualifiers |
| misc_feature | 1..687 |
|  | note = IgG4 Fc nucleic acid encoding sequence |
| source | 1..687 |
|  | mol_type = other DNA |
|  | organism = synthetic construct |

SEQUENCE: 8
```
gagtccaaat atggtccccc atgcccaccc tgcccagcac ctgaggccgc cggggggacca   60
tcagtcttcc tgttcccccc aaaacccaag gacactctca tgatctcccg gacccctgag  120
gtcacgtgcg tggtggtgga cgtgagccag gaagacccca ggtccagtt caactggtac  180
gtggatggcg tggaggtgca taatgccaag acaaagccgc gggaggagca gttcaacagc  240
acgtaccgtg tggtcagcgt cctcaccgtc ctgcaccagg actggctgaa cggcaaggag  300
tacaagtgca aggtctccaa caaaggcctc ccgtcctccc tcgagaaaac catctccaaa  360
gccaaagggc agccccgaga gccacaggtg tacaccctgc ccccatccca ggaggagatg  420
accaagaacc aggtcagcct gacctgcctg gtcaaaggct tctaccccag cgacatcgcc  480
gtggagtggg aaagcaatgg gcagccggag aacaactaca agaccacgcc tcccgtgctg  540
gactccgacg gctccttctt cctctacagc aggctaaccg tggacaagag caggtggcag  600
gaggggaatg tcttctcatg ctccgtgatg catgaggctc tgcacaacca ctacacacag  660
aagagcctct ccctgtctct gggttga                                     687
```

| SEQ ID NO: 9 | moltype = AA  length = 15 |
|---|---|
| FEATURE | Location/Qualifiers |
| REGION | 1..15 |
|  | note = Linker |
| source | 1..15 |
|  | mol_type = protein |
|  | organism = synthetic construct |

SEQUENCE: 9
```
GGGGSGGGGS GGGGS                                                   15
```

| SEQ ID NO: 10 | moltype = AA  length = 276 |
|---|---|
| FEATURE | Location/Qualifiers |
| REGION | 1..276 |
|  | note = GLP1-Fc amino acid sequence |
| source | 1..276 |
|  | mol_type = protein |
|  | organism = synthetic construct |

SEQUENCE: 10
```
HGEGTFTSDV SSYLEEQAAK EFIAWLVKGG GGGGSGGGG SGGGGSAESK YGPPCPSCPA    60
PEFLGGPSVF LFPPKPKDTL MISRTPEVTC VVVDVSQEDP EVQFNWYVDG VEVHNAKTKP  120
REEQFNSTYR VVSVLTVLHQ DWLNGKEYKC KVSNKGLPSS IEKTISKAKG QPREPQVYTL  180
PPSQEEMTKN QVSLTCLVKG FYPSDIAVEW ESNGQPENNY KTTPPVLDSD GSFAAYSRLT  240
VDKSRWQEGN VFSCSVMHEA LHNHYTQKSL SLSPGK                            276
```

| SEQ ID NO: 11 | moltype = DNA  length = 831 |
|---|---|
| FEATURE | Location/Qualifiers |
| misc_feature | 1..831 |
|  | note = GLP1-Fc nucleotide encoding sequence |
| source | 1..831 |
|  | mol_type = other DNA |
|  | organism = synthetic construct |

SEQUENCE: 11
```
catggcgaag ggacctttac cagtgatgta agttcttatt tggaagagca agctgccaag   60
gaattcattg cttggctggt gaaaggcggc ggaggcggag cggaagcgg aggcggagga  120
agcggcggtg cgcagcagcgc tgagtccaaa tatggtcccc catgcccagca          180
cctgagttcc tggggggacc atcagtcttc ctgttccccc caaaacccaa ggacactctc  240
atgatctccc ggacccctga ggtcacgtgc gtggtggtgg acgtgagcca ggaagacccc  300
gaggtccagt tcaactggta cgtggatggc gtggaggtgc ataatgccaa gacaaagccg  360
```

```
cgggaggagc agttcaacag cacgtaccgt gtggtcagcg tcctcaccgt cctgcaccag   420
gactggctga acggcaagga gtacaagtgc aaggtctcca acaaaggcct cccgtcctcc   480
atcgagaaaa ccatctccaa agccaaaggg cagccccgag agccacaggt gtacaccctg   540
cccccatccc aggaggagat gaccaagaac caggtcagcc tgacctgcct ggtcaaaggc   600
ttctacccca gcgacatcgc cgtggagtgg gagagcaatg gccagccgga gaacaactac   660
aagaccacgc ctcccgtgct ggactccgac ggctccttcg ccgcatacag caggctaacc   720
gtggacaaga gcaggtggca ggaggggaat gtcttctcat gctccgtgat gcatgaggct   780
ctgcacaacc actacacaca gaagagcctc tccctgtctc cgggtaaatg a            831

SEQ ID NO: 12              moltype = AA   length = 18
FEATURE                    Location/Qualifiers
REGION                     1..18
                           note = T2A amino acid sequence
source                     1..18
                           mol_type = protein
                           organism = synthetic construct
SEQUENCE: 12
EGRGSLLTCG DVEENPGP                                                  18

SEQ ID NO: 13              moltype = DNA   length = 54
FEATURE                    Location/Qualifiers
misc_feature               1..54
                           note = T2A nucleic acid encoding sequence
source                     1..54
                           mol_type = other DNA
                           organism = synthetic construct
SEQUENCE: 13
gagggcagag gaagtctgct aacatgcggt gacgtcgagg agaatcctgg acct          54

SEQ ID NO: 14              moltype = AA   length = 519
FEATURE                    Location/Qualifiers
REGION                     1..519
                           note = FGF21-GLP1-Fc amino acid sequence
source                     1..519
                           mol_type = protein
                           organism = synthetic construct
SEQUENCE: 14
MDSDETGFEH SGLWVSVLAG LLLGACQADS SPLLQFGGQV RQRYLYTDDA QQTEAHLEIR    60
EDGTVGGAAD QSPESLLQLK ALKPGVIQIL GVKTSRFLCQ RPDGALYGSL HFDPEACSFR   120
ELLLEDGYNV YQSEAHGLPL HCPGNKSPHR DPAPRGPCRF LPLPGLPPAL PEPPGILAPQ   180
PPDVGSSDPL AMVGPSQGRS PSYASEGRGS LLTCGDVEEN PGMRALLAR LLLCVLVVSD    240
SKGHGEGTFT SDVSSYLEEQ AAKEFIAWLV KGGGGGGGSG GGGSGGGGSA ESKYGPPCPS   300
CPAPEFLGGP SVFLFPPKPK DTLMISRTPE VTCVVVDVSQ EDPEVQFNWY VDGVEVHNAK   360
TKPREEQFNS TYRVVSVLTV LHQDWLNGKE YKCKVSNKGL PSSIEKTISK AKGQPREPQV   420
YTLPPSQEEM TKNQVSLTCL VKGFYPSDIA VEWESNGQPE NNYKTTPPVL DSDGSFAAYS   480
RLTVDKSRWQ EGNVFSCSVM HEALHNHYTQ KSLSLSPGK                          519

SEQ ID NO: 15              moltype = DNA   length = 1560
FEATURE                    Location/Qualifiers
misc_feature               1..1560
                           note = FGF21-GLP1-Fc nucleotide encoding sequence
source                     1..1560
                           mol_type = other DNA
                           organism = synthetic construct
SEQUENCE: 15
atggactcgg acgagaccgg gttcgagcac tcaggactgt gggtttctgt gctggctggt    60
cttctgctgg gagcctgcca ggcagactcc agtcctctcc tgcaattcgg ggccaagtc   120
cggcagcggt acctctacac agatgatgcc cagcagacag aagcccacct ggagatcagg   180
gaggatggga cggtgggggg cgctgctgac cagagccccg aaagtctcct gcagctgaaa   240
gccttgaagc cgggagttat tcaaatcttg ggagtcaaga catccaggtt cctgtgccaa   300
cggccagatg gggccctgta tggatcgctc cactttgacc ctgaggcctg cagcttccgg   360
gagctgcttc ttgaggacgg atacaatgtt taccagtccg aagcccacgg cctcccgctg   420
cactgcccag ggaacaagtc cccacaccgg gaccctgcac ccgaggacc atgccgcttc   480
ctgccactac caggcctgcc cccgcactc ccggagccct ccggaatcct ggctccacag   540
ccccccgatg tgggctcctc ggaccctctg gccatggtgg gacccttccc gggccgaagc   600
cccagctacg cttccgaggg cagaggaagt ctgctaacat gcggtgacgt cgaggagaat   660
cctggaccta tgagagccct gctggcgcgc ctgcttctct cgtcctggt cgtgagcgac   720
tccaaaggcc atggcgaagg gaccttttacc agtgatgtaa gttcttattt ggaagagcaa   780
gctgccaagg aattcattgc ttggctggtg aaaggcggag gaggcggagg cggaagcgga   840
ggcggaggaa cggcggtgg cggcagcgct gagtccaaat atggtccccc atgcccatca   900
tgcccagcac ctgagttcct gggggaccc tcagtcttcc tgttcccccc aaaacccaag   960
gacactctca tgatctcccg gacccctgag gtcacgtgcg tggtggtgga cgtgagccag  1020
gaagaccccg aggtccagtt caactggtac gtggatggcg tggaggtgca taatgccaag  1080
acaaagccgc gggaggagca gttcaacagc acgtaccgtg tggtcagcgt cctcaccgtc  1140
ctgcaccagg actggctgaa cggcaaggag tacaagtgca aggtctccaa caaaggcctc  1200
ccgtcctcca tcgagaaaac catctccaaa gccaaaggc agccccgaga gccacaggtg  1260
tacaccctgc ccccatccca ggaggagatg accaagaacc aggtcagcct gacctgcctg  1320
gtcaaaggct tctaccccag cgacatcgcc gtggagtggg agagcaatgg cagccggag   1380
aacaactaca agaccacgcc tcccgtgctg gactccgacg gctccttcgc cgcatacagc  1440
```

```
aggctaaccg tggacaagag caggtggcag gaggggaatg tcttctcatg ctccgtgatg    1500
catgaggctc tgcacaacca ctacacacag aagagcctct ccctgtctcc gggtaaatga    1560

SEQ ID NO: 16           moltype = DNA   length = 33
FEATURE                 Location/Qualifiers
misc_feature            1..33
                        note = Primer
source                  1..33
                        mol_type = other DNA
                        organism = synthetic construct
SEQUENCE: 16
cgcggatccg ccaccatgga ctcggacgag acc                                  33

SEQ ID NO: 17           moltype = DNA   length = 28
FEATURE                 Location/Qualifiers
misc_feature            1..28
                        note = Primer
source                  1..28
                        mol_type = other DNA
                        organism = synthetic construct
SEQUENCE: 17
acgcgtcgac tcatttaccc ggagacag                                        28

SEQ ID NO: 18           moltype = DNA   length = 20
FEATURE                 Location/Qualifiers
misc_feature            1..20
                        note = Primer
source                  1..20
                        mol_type = other DNA
                        organism = synthetic construct
SEQUENCE: 18
cactgtgacc tcgcagatcc                                                 20

SEQ ID NO: 19           moltype = DNA   length = 20
FEATURE                 Location/Qualifiers
misc_feature            1..20
                        note = Primer
source                  1..20
                        mol_type = other DNA
                        organism = synthetic construct
SEQUENCE: 19
ataggcagct tctccgcatc                                                 20

SEQ ID NO: 20           moltype = DNA   length = 18
FEATURE                 Location/Qualifiers
misc_feature            1..18
                        note = Primer
source                  1..18
                        mol_type = other DNA
                        organism = synthetic construct
SEQUENCE: 20
cctggcaccc agcacaat                                                   18

SEQ ID NO: 21           moltype = DNA   length = 18
FEATURE                 Location/Qualifiers
misc_feature            1..18
                        note = Primer
source                  1..18
                        mol_type = other DNA
                        organism = synthetic construct
SEQUENCE: 21
gggccggact cgtcatac                                                   18

SEQ ID NO: 22           moltype = AA    length = 20
FEATURE                 Location/Qualifiers
source                  1..20
                        mol_type = protein
                        organism = unidentified
SEQUENCE: 22
MRALLARLLL CVLVVSDSKG                                                 20
```

METHOD OF TREATING DIABETES WITH FGF21 AND GLP1 DOUBLE GENE-MODIFIED CELL

CROSS-REFERENCE

This application is a continuation application of U.S. application Ser. No. 16/954,763, filed Jun. 17, 2020, which is a U.S. national phase filing under 35 U.S.C. § 371 of International Application No. PCT/CN2018/081616, filed Apr. 2, 2018, which claims the benefit of Chinese Patent Application No. 201711374615.0, filed Dec. 19, 2017, each of which is incorporated herein by reference in its entirety.

SEQUENCE LISTING

The instant application contains a Sequence Listing which has been submitted electronically in XML format and is hereby incorporated by reference in its entirety. Said XML file, created on May 15, 2025, is named 57310-701301v2.xml and is 33,661 bytes in size.

TECHNICAL FIELD

The present invention relates to the field of cell therapy. Specifically, the present invention relates to a modified mesenchymal stem cell and a culture supernatant thereof, and a pharmaceutical composition comprising the cell or the culture supernatant thereof. The present invention also relates to use of the modified mesenchymal stem cell and the culture supernatant thereof in treating a metabolic disease in a subject (e.g., a human), and in preparing a medicament for treating a metabolic disease in a subject (e.g., a human). The present invention also relates to a method for treating a metabolic disease, comprising the step of administering to a subject in need thereof the modified mesenchymal stem cell of the present invention or the culture supernatant thereof, or the pharmaceutical composition thereof.

BACKGROUND

Metabolic diseases such as diabetes are closely related to some endogenous molecules involved in metabolic regulation. There are three major types of such endogenous molecules that have been discovered: hormones including insulin, glucagon, GLP1, glucocorticoids and the like; cell growth factors with hormone-like functions including FGF19, FGF21, and FGF23 and the like; and enzymes involved in metabolic regulation or cell signaling transduction including SPK1, PI3K, HSL and the like.

Insufficient secretion, decreased activity or functional deficiency of the endogenous hormones, cytokines or enzymes are closely associated with the occurrence of metabolic diseases. For example, resistance and relatively insufficient secretion of insulin are the key reasons of diabetes. Therefore, molecules essential for regulating the balance of glucose and lipid metabolism are also attractive targets for developing drugs for the treatment of metabolic syndromes such as diabetes. Among them, insulin and glucagon-like polypeptide 1 (GLP1) have currently become the most important drugs for treating diabetes.

At present, the hypoglycemic drugs developed for GLP1 are mainly inhibitors of DPP4 which inhibits the degradation of GLP1, and GLP1 analogs. GLP1-Fc obtained by fusion of GLP1 with human antibody Fc displays prolonged half-life and good tolerance. Fibroblast growth factor (FGF) is an important class of tissue growth factors, including 22 family members. FGF19/21/23 are a group of the members of the FGF family, which have hormone-like effects and play important roles in regulating glucose and lipid metabolism. FGF21 is mainly synthesized by liver, and acts on adipose tissue through the endocrine pathway to regulate the metabolism of glucose and lipids. As a molecule regulating glucose and lipid metabolism, FGF21 has been developed as a drug for treating metabolic diseases. However, in clinical applications, GLP1-Fc and FGF21 both need to be administrated to the patient for long term or even for life time. In addition, GLP1-Fc and FGF21 may also need to be used in combinational administration, as they could only relieve symptoms of the diseases, but not fundamentally eliminate the cause of the diseases.

In view of the deficiencies of the currently available hypoglycemic and lipid-lowering drugs, a novel, reliable approach which can treat the metabolic disease fundamentally is in huge demand.

SUMMARY

After intensive experiments and repeated explorations, the inventors of the present application surprisingly discovered that mesenchymal stem cells with modified FGF21 and GLP-1 genes show significant activities of lowering blood glucose and blood lipids. Based on this finding, the present invention provides a novel modified cell for treating metabolic diseases, and a novel treatment method of metabolic diseases by using the cell.

Modified Mesenchymal Stem Cell

In one aspect, the present invention provides a modified mesenchymal stem cell which expresses: (1) a first protein selected from FGF21 or a variant thereof, or a first fusion protein comprising the FGF21 or the variant thereof; and (2) a second protein selected from GLP-1 or a variant thereof, or a second fusion protein comprising the GLP-1 or the variant thereof.

In certain preferred embodiments, the variant of FGF21 has one or more amino acid substitutions, insertions, or deletions compared to the sequence which it is derived from, or has at least 80%, 85%, 90%, 95%, 96%, 97%, 98%, or 99% sequence identity with the sequence which it is derived from, and retains FGF21 activity.

As used herein, the "FGF21 activity" refers to one or more physiological functions of naturally occurring FGF21 which are well known to those skilled in the art, including but not limited to inducing insulin-independent glucose uptake, reducing levels of plasma glucose, fructosamine, triglyceride, insulin, and glucagon, reducing LDL cholesterol and increasing HDL cholesterol, enhancing insulin sensitivity and the like. Details of the functions can be found in, e.g., Dostálová I., et al. Physiol Res. 2009; 58 (1): 1-7; Kharitonenkov A., et al. J Clin Invest. 2005 June; 115 (6): 1627-35.

In certain preferred embodiments, the variant of GLP-1 has one or more amino acid substitutions, insertions, or deletions compared to the sequence which it is derived from, or has at least 80%, 85%, 90%, 95%, 96%, 97%, 98%, or 99% sequence identity with the sequence which it is derived from, and retains GLP-1 activity.

As used herein, the "GLP-1 activity" refers to one or more physiological functions of naturally occurring GLP-1 which are known to those skilled in the art, including but not limited to glucose dependent stimulation of insulin secretion, inhibition of glucagon secretion, stimulation of (pro) insulin biosynthesis, reducing food intake, deceleration of gastric emptying and the like. Details of the functions can be found in, e.g., Nauck M A, et al. Exp Clin Endocrinol Diabetes. 1997; 105 (4): 187-95.

In certain preferred embodiments, the FGF21 has an amino acid sequence as shown in SEQ ID NO: 1.

In certain preferred embodiments, the GLP-1 has an amino acid sequence as shown in SEQ ID NO: 4.

In certain preferred embodiments, the modified mesenchymal stem cell expresses: (1) a first protein selected from an amino acid sequence as shown in SEQ ID NO: 2, or a first fusion protein comprising the amino acid sequence as shown in SEQ ID NO: 2; and (2) a second protein selected from an amino acid sequence as shown in SEQ ID NO: 5, or a second fusion protein comprising the amino acid sequence as shown in SEQ ID NO: 5.

In certain preferred embodiments, the modified mesenchymal stem cell is capable of secreting the first protein and the second protein.

In certain preferred embodiments, the first fusion protein further comprises a first additional polypeptide. In certain preferred embodiments, the first additional polypeptide is capable of extending the half-life of the first fusion protein in vivo.

In certain preferred embodiments, the first additional polypeptide is selected from an immunoglobulin Fc domain (e.g., a human immunoglobulin Fc domain, such as an Fc domain of human IgG), a serum albumin (e.g., a human serum albumin (HSA)), an albumin binding polypeptide (e.g., an HSA binding polypeptide), a transferrin, and a functional fragment thereof.

In certain preferred embodiments, the first additional polypeptide is a human immunoglobulin Fc domain, for example, an Fc domain of human IgG, such as an Fc domain of human IgG1, IgG2, IgG3, or IgG4. In certain exemplary embodiments, the first additional polypeptide has an amino acid sequence as shown in SEQ ID NO: 7.

In certain preferred embodiments, the first additional polypeptide is fused with the FGF21 or the variant thereof optionally via a linker. In certain preferred embodiments, the first additional polypeptide is fused with the N-terminus or C-terminus of the FGF21 or the variant thereof optionally via a linker. In certain preferred embodiments, the linker is a peptide linker rich in a combination of Gly and Ser, such as a sequence consisting of repeated GGGGS amino acid sequences. In certain exemplary embodiments, the linker is GGGGSGGGGSGGGGS (SEQ ID NO: 9).

In certain preferred embodiments, the second fusion protein further comprises a second additional polypeptide. In certain preferred embodiments, the second additional polypeptide is capable of extending the half-life of the second fusion protein in vivo.

In certain preferred embodiments, the second additional polypeptide is selected from the group consisting of an immunoglobulin Fc domain (e.g., a human immunoglobulin Fc domain, such as an Fc domain of human IgG), a serum albumin (e.g., a human serum albumin (HSA)), an albumin binding polypeptide (e.g., an HSA binding polypeptide), a transferrin, and a functional fragment thereof.

In certain preferred embodiments, the second additional polypeptide is a human immunoglobulin Fc domain, for example, an Fc domain of human IgG, such as an Fc domain of human IgG1, IgG2, IgG3, or IgG4. In certain exemplary embodiments, the second additional polypeptide has an amino acid sequence as shown in SEQ ID NO: 7.

In certain preferred embodiments, the second additional polypeptide is fused with the GLP-1 or the variant thereof optionally via a linker. In certain preferred embodiments, the second additional polypeptide is fused with the N-terminus or C-terminus of the GLP-1 or the variant thereof optionally via a linker. In certain preferred embodiments, the linker is a peptide linker rich in a combination of Gly and Ser, such as a sequence consisting of repeated GGGGS amino acid sequences. In certain exemplary embodiments, the linker is GGGGSGGGGSGGGGS (SEQ ID NO: 9).

In certain exemplary embodiments, the modified mesenchymal stem cell expresses: (1) a first protein selected from an amino acid sequence as shown in SEQ ID NO: 2, or a first fusion protein comprising the amino acid sequence as shown in SEQ ID NO: 2; and (2) a second protein selected from an amino acid sequence as shown in SEQ ID NO: 5, or a second fusion protein comprising the amino acid sequence as shown in SEQ ID NO: 5.

In certain exemplary embodiments, the modified mesenchymal stem cell expresses an amino acid sequence as shown in SEQ ID NO: 2, and an amino acid sequence as shown in SEQ ID NO: 10.

In certain preferred embodiments, the modified mesenchymal stem cell comprises:
(1) a first exogenous nucleic acid comprising a nucleotide sequence encoding the first protein; and
(2) a second exogenous nucleic acid comprising a nucleotide sequence encoding the second protein.

In certain preferred embodiments, the first exogenous nucleic acid and/or the second exogenous nucleic acid is operably linked to a promoter (e.g., a constitutive promoter, a tissue-specific promoter, or an inducible promoter).

In certain preferred embodiments, the first exogenous nucleic acid and/or the second exogenous nucleic acid is linked with a nucleotide sequence encoding a signal peptide. In certain exemplary embodiments, the 5' end of the second exogenous nucleic acid is linked with a nucleotide sequence encoding a signal peptide (e.g., a signal peptide as shown in SEQ ID NO: 22).

In certain preferred embodiments, the first exogenous nucleic acid and the second exogenous nucleic acid may be linked by a sequence encoding a self-cleaving peptide. In certain exemplary embodiments, the sequence encoding the self-cleaving peptide is linked to the 3' end of the first exogenous nucleic acid, and to the 5' end of the second exogenous nucleic acid.

In certain preferred embodiments, the first exogenous nucleic acid and/or the second exogenous nucleic acid are integrated into the genome of the mesenchymal stem cell.

In certain preferred embodiments, the first exogenous nucleic acid and/or the second exogenous nucleic acid is separated from the genome of the mesenchymal stem cell. In such embodiments, the modified mesenchymal stem cell comprises an expression vector, and the first exogenous nucleic acid and the second exogenous nucleic acid are comprised in the same or different expression vectors.

In an exemplary embodiment, the expression vector comprises the first exogenous nucleic acid and the second exogenous nucleic acid. In such embodiments, the first exogenous nucleic acid and the second exogenous nucleic acid may be linked by a sequence encoding a self-cleaving peptide. In certain exemplary embodiments, the sequence encoding the self-cleaving peptide is linked to the 3' end of the first exogenous nucleic acid, and to the 5' end of the second exogenous nucleic acid.

In the present invention, suitable self-cleaving peptides are known to those skilled in the art, and examples of the self-cleaving peptides include, but are not limited to, 2A peptides derived from aphtho- and cardiovirus, such as, 2A peptides derived from foot-and-mouth disease virus (FMDV), equine rhinitis A virus (ERAV), Thoseaasigna virus (TaV), or porcine teschovirus (PTV-1).

In certain preferred embodiments, the first exogenous nucleic acid and the second exogenous nucleic acid are linked by a sequence encoding a 2A peptide. In certain exemplary embodiments, the sequence encoding the 2A peptide is linked to the 3' end of the first exogenous nucleic acid, and to the 5' end of the second exogenous nucleic acid. In certain preferred embodiments, the 2A peptide is a 2A peptide derived from Thoseaasigna virus (TaV). In certain exemplary embodiments, the 2A peptide has an amino acid sequence as shown in SEQ ID NO: 12. In certain exemplary embodiments, the sequence encoding the 2A peptide has a nucleotide sequence as shown in SEQ ID NO: 13.

In the present invention, mesenchymal stem cells can be genetically modified by methods and techniques well known in the art, such as, physical, chemical or biological methods, or a combination thereof. For example, the biological methods include the use of viral vectors, such as, lentivirus, retrovirus, pox virus, herpes simplex virus I, adenovirus and adeno-associated virus, etc. For example, the chemical methods include colloidal dispersion systems, such as, macromolecular complexes, nanocapsules, microspheres, beads and the like; lipid-based systems, including oil-in-water emulsions, micelles, mixed micelles, or liposomes, etc. For example, the physical methods include calcium phosphate precipitation, lipid transfection, particle bombardment, microinjection, electroporation and the like.

In certain preferred embodiments, the modified mesenchymal stem cell of the present invention is obtained by introducing the first exogenous nucleic acid and the second exogenous nucleic acid into a mesenchymal stem cell.

In certain preferred embodiments, the modified mesenchymal stem cell is obtained by the following steps:
(1) providing an expression vector comprising the first exogenous nucleic acid and the second exogenous nucleic acid;
(2) transfecting the expression vector in step (1) into a mesenchymal stem cell.

In certain preferred embodiments, in step (2), the expression vector is stably transfected into the mesenchymal stem cell. In certain preferred embodiments, in step (1), the expression vector is a viral vector, such as a lentiviral vector. In certain preferred embodiments, the expression vector comprises the nucleotide sequence as shown in SEQ ID NO: 15.

In certain preferred embodiments, the mesenchymal stem cell is derived from adipose tissue, umbilical cord, bone marrow or cord blood. In certain exemplary embodiments, the mesenchymal stem cell is derived from adipose tissue.

The modified mesenchymal stem cell of the present invention can be formulated and administered as a pharmaceutical composition. Such pharmaceutical composition may be in any form known in the medical field, and is preferably an injection (including injection solution, lyophilized powder). In certain preferred embodiments, the pharmaceutical composition comprises a pharmaceutically acceptable sterile isotonic aqueous or non-aqueous solution (e.g., a balanced salt solution or physiological saline), dispersion, suspension, or emulsion. General principles of formulating the pharmaceutical composition can be found in Cell Therapy: Stem Cell Transplantation, Gene Therapy, and Cellular Immunotherapy, edited by G. Morstyn and W. Sheridan, Cambridge University Press, 1996; and Hematopoietic Stem Cell Therapy, E. D. Ball, J. Lister & P. Law, Churchill Livingstone, 2000.

In certain preferred embodiments, the modified mesenchymal stem cell of the present invention is used to treat a metabolic disease in a subject, or to prepare a medicament for treating a metabolic disease in a subject.

In certain preferred embodiments, the metabolic disease is selected from obesity, type I and type II diabetes, dyslipidemia (e.g., hyperlipidemia), non-alcoholic fatty liver disease (NAFLD), non-alcoholic steatohepatitis (NASH), insulin resistance, hyperinsulinemia, glucose intolerance, hyperglycemia, metabolic syndrome, atherosclerosis, coronary heart disease, hypertension and other metabolic diseases, and secondary complications thereof (e.g., diabetic complications, such as retinopathy, neuropathy, kidney disease, and delayed wound healing).

In certain preferred embodiments, the subject is a mammal, such as a human.

Culture and Culture Supernatant

In another aspect, the present invention provides a culture comprising the modified mesenchymal stem cell of the present invention, and a culture medium.

In the present invention, the culture medium that can be used for culturing stem cells is known to those skilled in the art, and non-limiting examples of the culture medium include α-MEM culture medium, DMEM culture medium, IMDM culture medium, Ham's F12 culture medium, RPMI1640 culture medium, and a mixed culture medium formed by any combination thereof (e.g., an IMDM/HamF12 culture medium made by mixing equal amounts of IMDM and HamF12). The above-mentioned culture medium optionally further comprises supplementary substances, such as, serum (such as, fetal bovine serum, human serum, sheep serum and the like), serum replacements (such as, Knockout serum replacement (KSR) and the like), bovine serum albumin (BSA), antibiotics, vitamins, and minerals.

In certain exemplary embodiments, the culture medium is an α-MEM culture medium with or without serum.

The culture of the present invention can be formulated and administered as a pharmaceutical composition. Such pharmaceutical composition may be in any form known in the medical field, and is preferably an injection (including injection solution, lyophilized powder). In certain preferred embodiments, the pharmaceutical composition comprises a pharmaceutically acceptable sterile isotonic aqueous or non-aqueous solution (e.g., a balanced salt solution or physiological saline), dispersion, suspension, or emulsion. General principles of formulating the pharmaceutical composition can be found in Cell Therapy: Stem Cell Transplantation, Gene Therapy, and Cellular Immunotherapy, edited by G. Morstyn and W. Sheridan, Cambridge University Press, 1996; and Hematopoietic Stem Cell Therapy, E. D. Ball, J. Lister & P. Law, Churchill Livingstone, 2000.

In certain preferred embodiments, the culture as described herein is used to treat a metabolic disease in a subject, or to prepare a medicament for treating a metabolic disease in a subject.

In certain preferred embodiments, the metabolic disease is selected from obesity, type I and type II diabetes, dyslipidemia (e.g., hyperlipidemia), non-alcoholic fatty liver disease (NAFLD), non-alcoholic steatohepatitis (NASH), insulin resistance, hyperinsulinemia, glucose intolerance, hyperglycemia, metabolic syndrome, atherosclerosis, coronary heart disease, hypertension and other metabolic diseases, and secondary complications thereof (e.g., diabetic complications, such as retinopathy, neuropathy, kidney disease, and delayed wound healing).

In certain preferred embodiments, the subject is a mammal, such as a human.

In another aspect, the present invention provides culture supernatant, which is the supernatant of the culture of the present invention.

In certain preferred embodiments, the culture supernatant is free of the modified mesenchymal stem cell.

In certain preferred embodiments, the culture supernatant is free of serum.

In certain preferred embodiments, the culture supernatant comprises a basal culture medium, or a culture medium supplemented with one or more supplementary substances (e.g., serum). The basal culture medium optionally further comprises one or more supplementary substances (e.g., serum). In certain exemplary embodiments, the culture supernatant comprises an α-MEM culture medium with or without serum.

The culture supernatant of the present invention can be formulated and administered as a pharmaceutical composition. Such pharmaceutical compositions may be in any form known in the medical field, such as, tablets, pills, suspensions, emulsions, solutions, gels, capsules, powders, granules, elixirs, lozenges, suppositories, injections (including injection solution, lyophilized powder) and other forms.

In certain preferred embodiments, the culture supernatant as described herein is used to treat a metabolic disease in a subject, or to prepare a medicament for treating a metabolic disease in a subject.

In certain preferred embodiments, the metabolic disease is selected from obesity, type I and type II diabetes, dyslipidemia (e.g., hyperlipidemia), non-alcoholic fatty liver disease (NAFLD), non-alcoholic steatohepatitis (NASH), insulin resistance, hyperinsulinemia, glucose intolerance, hyperglycemia, metabolic syndrome, atherosclerosis, coronary heart disease, hypertension and other metabolic diseases, and secondary complications of these diseases (e.g., diabetic complications, such as retinopathy, neuropathy, kidney disease, and delayed wound healing).

In certain preferred embodiments, the subject is a mammal, such as a human.

In another aspect, the present invention also relates to a method for preparing the culture supernatant as described herein comprising the following steps:
(1) culturing the modified mesenchymal stem cell of the present invention; and
(2) recovering the supernatant of the culture obtained in step (1).

In certain preferred embodiments, the method further comprises: (3) treating the supernatant obtained in step (2), and the treatment is selected from centrifuge, concentration, solvent replacement, dialysis, freezing, drying, freeze-drying, dilution, desalting, preservation, and any combination thereof.

In the present invention, the modified mesenchymal stem cell of the present invention can be cultured using any culture medium and culture conditions known in the art for culturing stem cells. In certain preferred embodiments, a basal culture medium may be used in step (1). The basal culture medium optionally comprises one or more supplementary substances (e.g., serum).

In certain preferred embodiments, the basal culture medium is selected from α-MEM culture medium, DMEM culture medium, IMDM culture medium, Ham's F12 culture medium, RPMI1640 culture medium, and a mixed culture medium formed by any combination thereof (e.g., an IMDM/HamF12 culture medium made by mixing equal amounts of IMDM and HamF12). In certain preferred embodiments, the supplementary substances may be selected from serum (such as, fetal bovine serum, human serum, sheep serum and the like), serum replacements (such as, Knockout serum replacement (KSR) and the like), bovine serum albumin (BSA), antibiotics, vitamins, and minerals.

In certain exemplary embodiments, the modified mesenchymal stem cells are cultured using an α-MEM culture medium with or without serum in step (1).

In certain preferred embodiments, the culture supernatant of the present invention is free of serum to improve safety. Therefore, in certain exemplary embodiments, the modified mesenchymal stem cell may be cultured using a culture medium free of serum (e.g., a basal culture medium or a serum-free culture medium), so as to obtain a culture supernatant free of serum. In such embodiments, the culture medium free of serum can be used throughout the culturing process, or in the last or last few subcultures. In certain exemplary embodiments, the culture supernatant obtained in step (2) may be subjected to dialysis or solvent replacement to remove serum, and in this way a culture supernatant free of serum may also be obtained.

Pharmaceutical Composition and Therapeutic Use

In another aspect, the present invention provides a pharmaceutical composition comprising the modified mesenchymal stem cell, the culture, or the culture supernatant as described herein.

In certain preferred embodiments, the pharmaceutical composition comprises a therapeutically effective amount of the modified mesenchymal stem cell or the culture.

In certain preferred embodiments, the pharmaceutical composition comprises one or more of the modified mesenchymal stem cells as described herein.

In certain preferred embodiments, the pharmaceutical composition may be in any form known in the medical field. For example, the pharmaceutical composition may be tablets, pills, suspensions, emulsions, solutions, gels, capsules, powders, granules, elixirs, lozenges, suppositories, injections (including injection solution, lyophilized powder) and other forms. In certain preferred embodiments, the pharmaceutical composition is an injection (including injection solution, lyophilized powder).

In certain preferred embodiments, the pharmaceutical composition further comprises a pharmaceutically acceptable carrier or excipient. In certain preferred embodiments, the pharmaceutical composition comprises a pharmaceutically acceptable sterile isotonic aqueous or non-aqueous solution (e.g., a balanced salt solution or physiological saline), dispersion, suspension, or emulsion.

In certain preferred embodiments, the pharmaceutical composition can be transplanted in the form of suspension, gel, colloid, slurry, or mixture.

General principles of formulating the pharmaceutical compositions containing the modified mesenchymal stem cell of the present invention can be found in Cell Therapy: Stem Cell Transplantation, Gene Therapy, and Cellular Immunotherapy, edited by G. Morstyn and W. Sheridan, Cambridge University Press, 1996; and Hematopoietic Stem Cell Therapy, E. D. Ball, J. Lister & P. Law, Churchill Livingstone, 2000.

In certain preferred embodiments, the pharmaceutical composition comprises a therapeutically effective amount of the culture supernatant as described herein.

In certain preferred embodiments, the pharmaceutical composition may be in any form known in the medical field. For example, the pharmaceutical composition may be tablets, pills, suspensions, emulsions, solutions, gels, capsules, powders, granules, elixirs, lozenges, suppositories, injections (including injection solution, lyophilized powder) and other forms. In certain preferred embodiments, the pharmaceutical composition is an injection (including injection solution, lyophilized powder).

In certain preferred embodiments, the pharmaceutical composition further comprises a pharmaceutically acceptable carrier or excipient. In certain preferred embodiments, the pharmaceutical composition comprises a pharmaceutically acceptable sterile isotonic aqueous or non-aqueous solution (e.g., a balanced salt solution or physiological saline), dispersion, suspension, or emulsion.

In certain preferred embodiments, the pharmaceutical composition of the present invention optionally further comprises an additional pharmaceutically active agent. In certain preferred embodiments, the additional pharmaceutically active agent is selected from anti-diabetic drugs, anti-obesity drugs, anti-hypertensive drugs, anti-atherosclerotic drugs, and lipid-lowering drugs.

In the present invention, non-limiting examples of suitable anti-diabetic drugs include thiazolidinediones (e.g., rosiglitazone or pioglitazone), biguanides (e.g., metformin or phenformin), sulfonylureas (e.g., glimepiride, glibenclamide, gliclazide, chlorpropamide or glipizide), glucosidase inhibitors (e.g., acarbose or miglitol), PPAR-α agonists, PPAR-γ agonists, PPAR-α/γ dual agonists (e.g., muraglitazar), aP2 inhibitors, DPP4 inhibitors (e.g., sitagliptin or vildagliptin), insulin sensitizers, insulin or megliginides (e.g., repaglinide) and the like.

Non-limiting examples of suitable anti-obesity drugs include β3 adrenergic agonists (e.g., AJ9677 (Takeda/Dainippon), L750355 (Merck) or CP331648 (Pfizer)), lipase inhibitors (e.g., orlistat), 5-hydroxytryptamine (and dopamine) reuptake inhibitors (e.g., sibutramine or topiramate), thyroid receptor beta compounds (e.g., the compounds disclosed in WO99/00353 and WO 00/039077), CB-1 antagonists (e.g., rimonabant) or anorectic drugs (e.g., dextroamphetamine).

Non-limiting examples of suitable lipid-lowering drugs (including anti-atherosclerotic drugs) include MTP inhibitors, cholesteryl ester transfer protein inhibitors (e.g., CP-529414 (Pfizer)), HMG CoA reductase inhibitors (e.g., pravastatin, lovastatin, simvastatin, atorvastatin, fluvastatin, cerivastatin, or alorvastin), squalene synthase inhibitors (e.g., the α-phosphono-sulfonate disclosed in U.S. Pat. No. 5,712,396), phenylacetic acid derivatives (e.g., fenofibrate, gemfibrozil, clofibrate, bezafibrate, ciprofibrate, clinofibrate, etc.), upregulators of LDL receptor activity (e.g., MD-700 (Taisho Pharmaceutical Co. Ltd) and LY295427 (Eli Lilly)), lipoxygenase inhibitors (e.g., the benzimidazole derivatives disclosed in WO 97/12615, the 15-LO inhibitors disclosed in WO 97/12613, and the isothiazolones disclosed in WO 96/38144), ACAT inhibitors (e.g., avasimibe), cholesterol absorption inhibitors, and ileal Na<+>/bile acid cotransporter inhibitors.

Non-limiting examples of suitable anti-hypertensive drugs include β adrenergic blockers, calcium channel blockers (e.g., diltiazem, verapamil, nifedipine, amlodipine), diuretics (e.g., chlorothiazide, hydrochlorothiazide, flumethiazide, hydroflumethiazide, bendroflumethiazide, methylchlorothiazide, trichlormethiazide, polythiazide, benzthiazide, tienilic acid, chlorthalidone, furosemide, bumetanide, amiloride or spironolactone), renin inhibitors, ACE inhibitors (e.g. captopril, zofenopril, fosinopril, enalapril, cilazpril, delapril, pentopril, quinapril, ramipril or lisinopril), AT-1 receptor antagonists (e.g., losartan, irbesartan, or valsartan), ET receptor antagonists (e.g., sitaxsentan or atrasentan), dual ET/AII antagonists (e.g., the compound disclosed in WO 00/01389), dual NEP-ACE inhibitors (e.g., omapatrilat), and nitrate esters.

In certain preferred embodiments, the pharmaceutical composition is used to treat a metabolic disease in a subject.

In certain preferred embodiments, the subject is a mammal, such as a human.

In certain preferred embodiments, the metabolic disease is selected from obesity, type I and type II diabetes, dyslipidemia (e.g., hyperlipidemia), non-alcoholic fatty liver disease (NAFLD), non-alcoholic steatohepatitis (NASH), insulin resistance, hyperinsulinemia, glucose intolerance, hyperglycemia, metabolic syndrome, atherosclerosis, coronary heart disease, hypertension and other metabolic diseases, and secondary complications of these diseases (e.g., diabetic complications, such as retinopathy, neuropathy, kidney disease, and delayed wound healing).

In another aspect, the present invention relates to use of the modified mesenchymal stem cell, the culture or the culture supernatant as described herein in treating a metabolic disease in a subject, or in preparing a medicament for treating a metabolic disease in a subject.

In certain preferred embodiments, the medicament comprises a therapeutically effective amount of the modified mesenchymal stem cells or the culture.

In certain preferred embodiments, the modified mesenchymal stem cells of the present invention may be used in combination. Therefore, the medicament may include one or more of the modified mesenchymal stem cells of the present invention.

In certain preferred embodiments, the medicament may be in any form known in the medical field. For example, the medicament may be tablets, pills, suspensions, emulsions, solutions, gels, capsules, powders, granules, elixirs, lozenges, suppositories, injections (including injection solution, lyophilized powder) and other forms. In certain preferred embodiments, the medicament is an injection (including injection solution, lyophilized powder).

In certain preferred embodiments, the medicament further comprises a pharmaceutically acceptable carrier or excipient. In certain preferred embodiments, the medicament comprises a pharmaceutically acceptable sterile isotonic aqueous or non-aqueous solution (e.g., a balanced salt solution or physiological saline), dispersion, suspension, or emulsion.

In certain preferred embodiments, the medicament can be transplanted in the form of suspension, gel, colloid, slurry, or mixture.

In certain preferred embodiments, the medicament comprises a therapeutically effective amount of the culture supernatant as described herein.

In certain preferred embodiments, the medicament may be in any form known in the medical field, such as tablets, pills, suspensions, emulsions, solutions, gels, capsules, powders, granules, elixirs, lozenges, suppositories, injections (including injection solution, lyophilized powder) and other forms. In certain preferred embodiments, the medicament is an injection (including injection solution, lyophilized powder).

In certain preferred embodiments, the medicament further comprises a pharmaceutically acceptable carrier or excipient. In certain preferred embodiments, the medicament comprises a pharmaceutically acceptable sterile isotonic aqueous or non-aqueous solution (e.g., a balanced salt solution or physiological saline), dispersion, suspension, or emulsion.

In certain preferred embodiments, the medicament optionally further comprises an additional pharmaceutically active agent. In certain preferred embodiments, the additional pharmaceutically active agent is selected from anti-diabetic drugs, anti-obesity drugs, anti-hypertensive drugs, anti-atherosclerotic drugs, and lipid-lowering drugs.

In certain preferred embodiments, the metabolic disease is selected from obesity, type I and type II diabetes, dyslipidemia (e.g., hyperlipidemia), non-alcoholic fatty liver disease (NAFLD), non-alcoholic steatohepatitis (NASH), insulin resistance, hyperinsulinemia, glucose intolerance, hyperglycemia, metabolic syndrome, atherosclerosis, coronary heart disease, hypertension and other metabolic diseases, and secondary complications thereof (e.g., diabetic complications, such as retinopathy, neuropathy, kidney disease, and delayed wound healing).

In certain preferred embodiments, the subject is a mammal, such as a human.

In another aspect, the present invention provides a method for treating a metabolic disease, comprising administering to a subject in need thereof the modified mesenchymal stem cell, the culture, the culture supernatant of the present invention, or the pharmaceutical composition of the present invention.

In certain preferred embodiments, the modified mesenchymal stem cells of the present invention may be used in combination. Thus, one or more of the modified mesenchymal stem cells of the present invention may be administered to a subject.

In certain preferred embodiments, the modified mesenchymal stem cell or the culture of the present invention can be formulated and administered as a pharmaceutical composition. Such pharmaceutical composition may comprise a therapeutically effective amount of the modified mesenchymal stem cell or the culture. In certain preferred embodiments, the pharmaceutical composition may be in any form known in the medical field. For example, the pharmaceutical composition may be tablets, pills, suspensions, emulsions, solutions, gels, capsules, powders, granules, elixirs, lozenges, suppositories, injections (including injection solution, lyophilized powder) and other forms. In certain preferred embodiments, the pharmaceutical composition is an injection (including injection solution, lyophilized powder). In certain preferred embodiments, the pharmaceutical composition further comprises a pharmaceutically acceptable carrier or excipient. In certain preferred embodiments, the pharmaceutical composition comprises a pharmaceutically acceptable sterile isotonic aqueous or non-aqueous solution (e.g., a balanced salt solution or physiological saline), dispersion, suspension, or emulsion. General principles of formulating the pharmaceutical composition can be found in Cell Therapy: Stem Cell Transplantation, Gene Therapy, and Cellular Immunotherapy, edited by G. Morstyn and W. Sheridan, Cambridge University Press, 1996; and Hematopoietic Stem Cell Therapy, E. D. Ball, J. Lister & P. Law, Churchill Livingstone, 2000.

In the present invention, the modified mesenchymal stem cell or the culture as described herein, or the pharmaceutical composition comprising the modified mesenchymal stem cell or the culture, can be administered to a subject by various suitable means. In certain preferred embodiments, the modified mesenchymal stem cell or the pharmaceutical composition as described herein is administered to a subject by local injection transplantation (e.g., stereotactic intracerebral injection transplantation or local spinal cord injection transplantation), blood circulation route transplantation (e.g., intravenous injection transplantation or intraarterial injection transplantation), or cerebrospinal fluid route transplantation (e.g., lumbar puncture and subarachnoid injection transplantation) and other routes. Those skilled in the art know how to select an appropriate cell transplantation route according to the location and nature of the lesion and the like.

In certain preferred embodiments, the modified mesenchymal stem cell, the culture or the pharmaceutical composition of the present invention can be transplanted in the form of suspension, gel, colloid, slurry, or mixture.

In certain preferred embodiments, the culture supernatant of the present invention can be formulated and administered as a pharmaceutical composition. Such pharmaceutical composition may comprise a therapeutically effective amount of the culture supernatant. In certain preferred embodiments, the pharmaceutical composition may be in any form known in the medical field, such as, tablets, pills, suspensions, emulsions, solutions, gels, capsules, powders, granules, elixirs, lozenges, suppositories, injections (including injection solution, lyophilized powder) and other forms. In certain preferred embodiments, the pharmaceutical composition is an injection (including injection solution, lyophilized powder). In certain preferred embodiments, the pharmaceutical composition further comprises a pharmaceutically acceptable carrier or excipient. In certain preferred embodiments, the pharmaceutical composition comprises a pharmaceutically acceptable sterile isotonic aqueous or non-aqueous solution (e.g., a balanced salt solution or physiological saline), dispersion, suspension, or emulsion.

In the present invention, the culture supernatant of the present invention, or the pharmaceutical composition comprising the culture supernatant, can be administered to a subject by various suitable means. In certain preferred embodiments, the culture supernatant of the present invention, or the pharmaceutical composition comprising the culture supernatant, can be administered by intradermal injection, subcutaneous injection, intramuscular injection, intravenous injection, oral administration, and other routes.

In certain preferred embodiments, the method further comprises administering an additional pharmaceutically active agent selected from anti-diabetic drugs, anti-obesity drugs, anti-hypertensive drugs, anti-atherosclerotic drugs, and lipid-lowering drugs. This additional pharmaceutically active agent may be administered before, at the same time or after administration of the modified mesenchymal stem cell, the culture supernatant thereof or the pharmaceutical composition as described herein.

In certain preferred embodiments, the method further includes administering an additional therapy. This additional therapy may be any therapy known for metabolic diseases, such as, drug therapy, surgical treatment, and the like. This additional therapy can be administered before, concurrently with, or after administration of the method as described above.

In certain preferred embodiments, the subject is a mammal, such as a human.

In certain preferred embodiments, the metabolic disease is selected from obesity, type I and type II diabetes, dyslipidemia (e.g., hyperlipidemia), non-alcoholic fatty liver disease (NAFLD), non-alcoholic steatohepatitis (NASH), insulin resistance, hyperinsulinemia, glucose intolerance, hyperglycemia, metabolic syndrome, atherosclerosis, coronary heart disease, hypertension and other metabolic diseases, and secondary complications thereof (e.g., diabetic complications, such as retinopathy, neuropathy, kidney disease, and delayed wound healing).

Definition of Terms

In the present invention, unless otherwise stated, scientific and technical terms used herein have meanings commonly understood by those skilled in the art. In addition, the molecular genetics, nucleic acid chemistry, cell culture, biochemistry, cell biology and other operating steps used herein are all routine steps widely used in the corresponding field. Meanwhile, definitions and explanations of related terms are provided below, to obtain better understanding of the present invention.

As used herein, the term "exogenous nucleic acid" refers to an artificially introduced nucleotide sequence that is foreign to a non-genetically modified cell. Exogenous nucleic acid includes, but is not limited to, any gene or nucleotide sequence that is not found in the genome of the cell.

As used herein, the term "FGF21" refers to a member of the fibroblast growth factor (FGF) protein family. Its amino acid sequence can be found in, for example, GenBank accession number NP_061986.1, and the corresponding nucleotide sequence can be found in, for example, NCBI reference sequence number NM_019113.2.

In the present invention, the expression "variant of FGF21" refers to a protein with an amino acid sequence having one or more amino acid substitutions, insertions or deletions compared to the wild-type sequence which it is derived from, or having at least 60%, 80%, 85%, 90%, 95%, 96%, 97%, 98%, or 99% sequence identity with the wild-type sequence which it is derived from (e.g., the full-length sequence of wild-type FGF21, such as the amino acid sequence as shown in SEQ ID NO: 1), and retains "FGF21 activity". Therefore, the "variant of FGF21" described in the present invention also includes the truncated forms of the N-terminus and/or C-terminus of the wild-type protein. Non-limiting examples of the "variant of FGF21" include those described in Chinese patent applications CN200980130476.4, CN201180065381.6, CN201280057789.3 or CN201580070276.X, international patent applications WO2005/061712, WO2006/028595, WO2006/028714, WO2006/065582 or WO2008/121563. The "FGF21 activity" refers to one or more physiological functions of naturally occurring FGF21 which are well known to those skilled in the art, including but not limited to binding and activating FGF21 receptors such as inducing insulin-independent glucose uptake; reducing plasma glucose, fructosamine, triglyceride, insulin, and glucagon levels; reducing LDL cholesterol and increasing HDL cholesterol; enhancing insulin sensitivity, etc. Details of the functions can be found in, for example, Dostálová I., et al. Physiol Res. 2009; 58 (1): 1-7; Kharitonenkov A., et al. J Clin Invest. 2005 June; 115 (6): 1627-35.

As used herein, the term "GLP-1" refers to glucagon-like peptide-1. It is known in the art that GLP-1 is obtained by post-translational modification and is derived from glucagon preproprotein. The wild-type glucagon preproprotein has the sequence as shown in NCBI accession number NP_002045 and can be found in international patent applications WO98/19698 and WO87/06941A. GLP-1 is a fragment consisting of amino acid residues 92-128 of glucagon preproprotein. Endogenous cleavage between residues 6 and 7 of the GLP-1 wild-type sequence yields two active forms (naturally truncated forms): GLP-1(7-37)OH (the wild-type sequence thereof is as shown in SEQ ID NO: 4), and GLP-1(7-36)NH2 formed after further amidation of the terminus.

In the present invention, the expression "variant of GLP-1" refers to a protein with an amino acid sequence having one or more amino acid substitutions, insertions or deletions compared to the wild-type sequence which it is derived from, or having at least 60%, 80%, 85%, 90%, 95%, 96%, 97%, 98%, or 99% sequence identity with the wild-type sequence which it is derived from (e.g., the wild-type sequence of the active form GLP-1 (7-37) OH, such as the amino acid sequence as shown in SEQ ID NO: 4), and retains "GLP-1 activity". Therefore, the "variant of GLP-1" described in the present invention also includes the truncated forms of the N-terminus and/or C-terminus of the wild-type protein, such as the naturally truncated form of GLP-1 as described above. Non-limiting examples of the "variant of GLP-1" include those described in Chinese patent applications CN200910173888.8, CN201010508567.1. The "GLP-1 activity" refers to one or more physiological functions of naturally occurring GLP-1 which are known to those skilled in the art, including but not limited to binding and activating the GLP-1 receptor, such as glucose dependent stimulation of insulin secretion, inhibition of glucagon secretion, stimulation of (pro) insulin biosynthesis, reducing food intake; deceleration of gastric emptying and the like. Details of the functions can be found in, e.g., Nauck M A, et al. Exp Clin Endocrinol Diabetes. 1997; 105 (4): 187-95.

As used herein, the expression "extending the half-life of a protein in vivo" refers to the ability to prevent or slow the hydrolysis and enzymatic degradation of the protein in vivo, increase the half-life, and/or improve or change other pharmacokinetics or biophysical properties, including but not limited to increasing absorption rate, reducing toxicity, improving solubility, and reducing protein aggregation, and the like. Substances that can be used to extend half-life are well known to those skilled in the art, and non-limiting examples include the Fc domain of immunoglobulin, serum albumin, transferrin, and the like.

As used herein, the term "Fc domain" has the meaning commonly assigned to it in the field of immunology, and particularly refers to antibody fragments that do not contain two antigen-binding regions (Fab fragments) from the antibody. The Fc domain consists of two heavy chain constant regions of the antibody that are bound by non-covalent interactions and disulfide bonds. The Fc domain may comprise a hinge region and extend to the C-terminus of the antibody via the CH2 and CH3 domains. The Fc domain may also contain one or more glycosylation sites. The effector function of the Fc domain is usually mediated by interaction with the Fc receptor (FcγR) or by binding to C1q and a fixed complement. Binding to FcγR can lead to antibody-dependent cell-mediated cytotoxicity (ADCC), while binding to complement factors can lead to complement-dependent cytotoxicity (CDC). Therefore, it is important to minimize the effector function when only Fc domain is used for extending the half-life. For example, the Fc domain of an immunoglobulin subtype with a relatively low ability to bind FcγR and complement factors (e.g., Fc of IgG4), or introduction of mutations into the natural Fc domain (e.g., substitution of one or more amino acids) can be used to reduce effector function. Therefore, in the present invention, the term "Fc domain" includes a natural Fc or a variant thereof. The variant has one or more mutations (e.g., amino acid substitutions, insertions, or deletions) compared to the wild-type sequence from which it is derived, and the mutations may affect or participate in, or may not affect or participate in: (1) formation of disulfide bonds, (2) incompatibility with the selected host cells, (3) N-terminal heterogeneity when expressed in the selected host cells, (4) glycosylation, (5) interaction with a complement, (6) binding to an Fc receptor other than a salvage receptor, or (7) antibody-dependent cytotoxicity (ADCC).

As used herein, the term "linker" refers to a linear polypeptide formed by multiple amino acid residues linked via peptide bonds. The linker of the present invention may be a synthetic amino acid sequence, or a naturally occurring polypeptide sequence, such as a polypeptide having a hinge region function. Such linker polypeptides are well known in the art (see, e.g., Holliger, P., et al. (1993) Proc. Natl. Acad. Sci. USA 90:6444-6448; Poljak, R. J., et al. (1994) Structure 2: 1121-1123).

As used herein, the term "culture" refers to a product obtained after culturing a cell (e.g., the modified mesenchymal stem cell of the present invention) in a culture medium.

As used herein, the term "culture supernatant" refers to a culture solution that does not contain the cell itself, and is obtained by culturing the cell (e.g., the modified mesenchymal stem cells of the present invention). Therefore, for example, the culture supernatant that can be used for the present invention can be obtained by separating and removing cell components after the culture. The culture supernatant may also be subjected to other treatments, such as, centrifugation, concentration, solvent replacement, dialysis, freezing, drying, freeze-drying, dilution, desalting, preservation, and the like.

As used herein, the term "vector" refers to a nucleic acid vehicle into which a polynucleotide can be inserted. When a vector enables expression of a protein encoded by an inserted polynucleotide, the vector is referred to as an expression vector. A vector can be introduced into a host cell by transformation, transduction, or transfection, so that the genetic material elements carried by the vector can be expressed in the host cell. Vectors are well known to those skilled in the art and include, but are not limited to: plasmids; phagemids; cosmids; artificial chromosomes, such as, yeast artificial chromosomes (YAC), bacterial artificial chromosomes (BAC), or P1-derived artificial chromosomes (PAC); phages, such as, λ phage or M13 phage and animal viruses, etc. Animal viruses that can be used as vectors include, but are not limited to, retroviruses (including lentiviruses), adenoviruses, adeno-associated viruses, herpes viruses (e.g., herpes simplex virus), poxviruses, baculoviruses, papillomaviruses, and papovaviruses (e.g., SV40). A vector can contain a variety of elements that control expression, including, but not limited to, promoter sequences, transcription initiation sequences, enhancer sequences, selection elements, and reporter genes. In addition, the vector may also contain a replication initiation site.

As used herein, the term "promoter" has the meaning well known to those skilled in the art and refers to a non-coding nucleotide sequence located upstream of a gene and capable of initiating expression of a downstream gene. A constitutive promoter is a nucleotide sequence that, when operably linked to a polynucleotide that encodes or defines a gene product, under most or all physiological conditions of a cell, results in the generation of the gene product in the cell. An inducible promoter is a nucleotide sequence that, when operably linked to a polynucleotide that encodes or defines a gene product, results in the generation of the gene product in the cell essentially only when an inducer corresponding to the promoter is present in the cell. A tissue-specific promoter is a nucleotide sequence that, when operably linked to a polynucleotide that encodes or defines a gene product, results in the generation of the gene product in the cell essentially only when the cell is a cell of the tissue type to which the promoter corresponds.

As used herein, the term "pharmaceutically acceptable carrier or excipient" refers to a carrier and/or excipient that is pharmacologically and/or physiologically compatible with the subject and the active ingredient, which is well known in the art (see, e.g., Remington's Pharmaceutical Sciences. Edited by Gennaro A R, 19th ed. Pennsylvania: Mack Publishing Company, 1995) and include, but are not limited to: pH regulator, surfactants, ionic strength enhancers, reagents that maintain osmotic pressure, reagents that delay absorption, diluents, adjuvants, preservatives, and the like. For example, pH regulators include, but are not limited to phosphate buffer. Surfactants include, but are not limited to, cationic, anionic or non-ionic surfactants, e.g., Tween-80. Ionic strength enhancers include but are not limited to sodium chloride. Reagents that maintain osmotic pressure include, but are not limited to, saccharides, NaCl and analogs thereof. Reagents that delay absorption include, but are not limited to, monostearate and gelatin. Diluents include, but are not limited to, water, aqueous buffers (e.g., buffered saline), alcohols and polyols (e.g., glycerol), and the like. Adjuvants include, but are not limited to, aluminum adjuvants (e.g., aluminum hydroxide), Freund's adjuvants (e.g., complete Freund's adjuvant), and the like. Preservatives include, but are not limited to, various antibacterial and antifungal reagents, e.g., thimerosal, 2-phenoxyethanol, parabens, trichloro-tert-butanol, phenol, sorbic acid, and the like. In certain embodiments, the pharmaceutically acceptable carrier or excipient is a sterile isotonic aqueous or non-aqueous solution (e.g., a balanced salt solution or physiological saline), dispersion, suspension, or emulsion.

As used herein, the term "treatment" refers to treating or curing a disease (e.g., a metabolic disease), delaying the onset of the symptom of a disease (e.g., a metabolic disease), and/or delaying the development of a disease (e.g., a metabolic disease).

As used herein, the term "effective amount" refers to an amount sufficient to obtain or at least partially obtain a desired effect. The "effective amount for treating a disease" refers to an amount sufficient to cure or at least partially prevent a disease and complications thereof in a patient already suffering from the disease (e.g., metabolic disease). It is well within the ability of those skilled in the art to determine such an effective amount. For example, the amount effective for therapeutic use will depend on the severity of the disease to be treated, the overall state of the patient's own immune system, the general condition of the patient, such as, age, body weight and sex, the administration mode of the drug, and other treatments administered concurrently, etc.

As used herein, the term "subject" includes, but is not limited to, various animals, such as mammals, such as, bovines, equines, caprids, porcines, canines, felines, leporidae, rodents (e.g., mice or rats), non-human primates (e.g., macaques or cynomolgus monkeys), or humans. In certain embodiments, the subject (e.g., a human) has a metabolic disease, or is at risk of suffering from a metabolic disease.

Beneficial Effects of the Present Invention

Compared with the prior art, the modified mesenchymal stem cell of the present invention has significant advantages. In particular, the modified mesenchymal stem cell of the present invention shows a synergistic effect, and can significantly reduce the blood glucose, blood lipids, and body weight of test animals, and can be safely administered to human subjects without triggering immunogenic response. Therefore, the modified mesenchymal stem cell of the present invention can be used to treat metabolic diseases and have great clinical value.

The embodiments of the present invention will be described in detail below with reference to the drawings and examples, but those skilled in the art will understand that the following drawings and examples are only used to illustrate the present invention, rather than limiting the scope of the present invention. Various objects and advantageous aspects of the present invention will become apparent to those skilled in the art from the following detailed description of the drawings and preferred embodiments.

SEQUENCE INFORMATION

Figure 1:
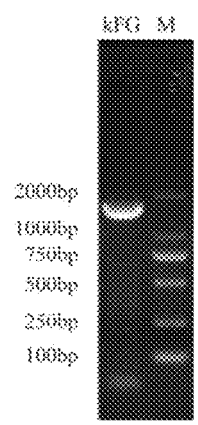
FIG. 1 shows the electrophoresis of the PCR amplified product, where M represents the Marker, and kFG represents the cloned FGF21/GLP1-Fc gene fragment.

Exemplary sequences of the present invention are provided in Table 1 below.

TABLE 1 description of sequences

| SEQ ID NO | Description | Sequence information |
|---|---|---|
| 1 | Wild-type full-length FGF21 sequence | MDSDETGFEHSGLWVSVLAGLLLGACQAHPIPDS SPLLQFGGQVRQRYLYTDDAQQTEAHLEIREDGT VGGAADQSPESLLQLKALKPGVIQILGVKTSRFLC QRPDGALYGSLHFDPEACSFRELLLEDGYNVYQS EAHGLPLHLPGNKSPHRDPAPRGPARFLPLPGLPP ALPEPPGILAPQPPDVGSSDPLSMVGPSQGRSPSYA S |
| 2 | FGF21v amino acid sequence | MDSDETGFEHSGLWVSVLAGLLLGACQADSSPLL QFGGQVRQRYLYTDDAQQTEAHLEIREDGTVGG AADQSPESLLQLKALKPGVIQILGVKTSRFLCQRP DGALYGSLHFDPEACSFRELLLEDGYNVYQSEAH GLPLHCPGNKSPHRDPAPRGPCRFLPLPGLPPALPE PPGILAPQPPDVGSSDPLAMVGPSQGRSPSYAS |
| 3 | FGF21v nucleotide sequence | ATGGACTCGGACGAGACCGGGTTCGAGCACTCA GGACTGTGGGTTTCTGTGCTGGCTGGTCTTCTGC TGGGAGCCTGCCAGGCAGACTCCAGTCCTCTCC TGCAATTCGGGGGCCAAGTCCGGCAGCGGTACC TCTACACAGATGATGCCCAGCAGACAGAAGCCC ACCTGGAGATCAGGGAGGATGGGACGGTGGGG GGCGCTGCTGACCAGAGCCCCGAAAGTCTCCTG CAGCTGAAAGCCTTGAAGCCGGGAGTTATTCAA ATCTTGGGAGTCAAGACATCCAGGTTCCTGTGC CAGCGGCCAGATGGGGCCCTGTATGGATCGCTC CACTTTGACCCTGAGGCCTGCAGCTTCCGGGAG CTGCTTCTTGAGGACGGATACAATGTTTACCAG TCCGAAGCCCACGGCCTCCCGCTGCACTGCCCA GGGAACAAGTCCCCACACCGGGACCCTGCACCC CGAGGACCATGCCGCTTCCTGCCACTACCAGGC CTGCCCCCCGCACTCCCGGAGCCACCCGGAATC CTGGCCCCCCAGCCCCCCGATGTGGGCTCCTCG |

TABLE 1-continued description of sequences

| SEQ ID NO | Description | Sequence information |
|---|---|---|
| | | GACCCTCTGGCCATGGTGGGACCTTCCCAGGGC CGAAGCCCCAGCTACGCTTCC |
| 4 | Wild-type GLP-1 (7-37)OH amino acid sequence | HAEGTFTSDVSSYLEGQAAKEFIAWLVKGRG |
| 5 | GLP-1v amino acid sequence | HGEGTFTSDVSSYLEEQAAKEFIAWLVKGGG |
| 6 | GLP-1v nucleotide sequence | CATGGCGAAGGGACCTTTACCAGTGATGTAAGT TCTTATTTGGAAGAGCAAGCTGCCAAGGAATTC ATTGCTTGGCTGGTGAAAGGCGGCGGA |
| 7 | Amino acid sequence of polypeptide for extending half-life (IgG4 Fc) | ESKYGPPCPPCPAPEAAGGPSVFLFPPKPKDTLMIS RTPEVTCVVVDVSQEDPEVQFNWYVDGVEVHNA KTKPREEQFNSTYRVVSVLTVLHQDWLNGKEYK CKVSNKGLPSSIEKTISKAKGQPREPQVYTLPPSQE EMTKNQVSLTCLVKGFYPSDIAVEWESNGQPENN YKTTPPVLDSDGSFFLYSRLTVDKSRWQEGNVFSC SVMHEALHNHYTQKSLSLSLG |
| 8 | Nucleotide sequence of polypeptide for extending half-life (IgG4 Fc) | GAGTCCAAATATGGTCCCCCATGCCCACCCTGC CCAGCACCTGAGGCCGCCGGGGGACCATCAGTC TTCCTGTTCCCCCCAAAACCCAAGGACACTCTC ATGATCTCCCGGACCCCTGAGGTCACGTGCGTG GTGGTGGACGTGAGCCAGGAAGACCCCGAGGT CCAGTTCAACTGGTACGTGGATGGCGTGGAGGT GCATAATGCCAAGACAAAGCCGCGGGAGGAGC AGTTCAACAGCACGTACCGTGTGGTCAGCGTCC TCACCGTCCTGCACCAGGACTGGCTGAACGGCA AGGAGTACAAGTGCAAGGTCTCCAACAAAGGC CTCCCGTCCTCCATCGAGAAAACCATCTCCAAA GCCAAAGGGCAGCCCCGAGAGCCACAGGTGTA CACCCTGCCCCCATCCCAGGAGGAGATGACCAA GAACCAGGTCAGCCTGACCTGCCTGGTCAAAGG CTTCTACCCCAGCGACATCGCCGTGGAGTGGGA AAGCAATGGGCAGCCGGAGAACAACTACAAGA CCACGCCTCCCGTGCTGGACTCCGACGGCTCCTT CTTCCTCTACAGCAGGCTAACCGTGGACAAGAG CAGGTGGCAGGAGGGGAATGTCTTCTCATGCTC CGTGATGCATGAGGCTCTGCACAACCACTACAC ACAGAAGAGCCTCTCCCTGTCTCTGGGTTGA |
| 9 | Linker | GGGGSGGGGSGGGGS |
| 10 | GLP1-Fc amino acid sequence | HGEGTFTSDVSSYLEEQAAKEFIAWLVKGGGGGG GSGGGGSGGGGSAESKYGPPCPSCPAPEFLGGPSV FLFPPKPKDTLMISRTPEVTCVVVDVSQEDPEVQF NWYVDGVEVHNAKTKPREEQFNSTYRVVSVLTV LHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFAAYSRLT VDKSRWQEGNVFSCSVMHEALHNHYTQKSLSLSP GK |
| 11 | GLP1-Fc nucleotide sequence | CATGGCGAAGGGACCTTTACCAGTGATGTAAGT TCTTATTTGGAAGAGCAAGCTGCCAAGGAATTC ATTGCTTGGCTGGTGAAAGGCGGCGGAGGCGGA GGCGGAAGCGGAGGCGGAGGAAGCGGCGGTGG CGGCAGCGCTGAGTCCAAATATGGTCCCCCATG CCCATCATGCCCAGCACCTGAGTTCCTGGGGGG ACCATCAGTCTTCCTGTTCCCCCCAAAACCCAA GGACACTCTCATGATCTCCCGGACCCCTGAGGT CACGTGCGTGGTGGTGGACGTGAGCCAGGAAG ACCCCGAGGTCCAGTTCAACTGGTACGTGGATG GCGTGGAGGTGCATAATGCCAAGACAAAGCCG CGGGAGGAGCAGTTCAACAGCACGTACCGTGT GGTCAGCGTCCTCACCGTCCTGCACCAGGACTGG CTGAACGGCAAGGAGTACAAGTGCAAGGTCTCC AACAAAGGCCTCCCGTCCTCCATCGAGAAAACC ATCTCCAAAGCCAAAGGGCAGCCCCGAGAGCC ACAGGTGTACACCCTGCCCCCATCCCAGGAGGA GATGACCAAGAACCAGGTCAGCCTGACCTGCCT |

TABLE 1-continued description of sequences

| SEQ ID NO | Description | Sequence information |
|---|---|---|
| | | GGTCAAAGGCTTCTACCCCAGCGACATCGCCGT<br>GGAGTGGGAGAGCAATGGGCAGCCGGAGAACA<br>ACTACAAGACCACGCCTCCCGTGCTGGACTCCG<br>ACGGCTCCTTCGCCGCATACAGCAGGCTAACCG<br>TGGACAAGAGCAGGTGGCAGGAGGGGAATGTC<br>TTCTCATGCTCCGTGATGCATGAGGCTCTGCACA<br>ACCACTACACACAGAAGAGCCTCTCCCTGTCTC<br>CGGGTAAATGA |
| 12 | T2A amino acid sequence | EGRGSLLTCGDVEENPGP |
| 13 | T2A nucleic acid sequence | GAGGGCAGAGGAAGTCTGCTAACATGCGGTGA<br>CGTCGAGGAGAATCCTGGACCT |
| 14 | FGF21-GLP1-Fc amino acid sequence | MDSDETGFEHSGLWVSVLAGLLLGACQADSSPLL<br>QFGGQVRQRYLYTDDAQQTEAHLEIREDGTVGG<br>AADQSPESLLQLKALKPGVIQILGVKTSRFLCQRP<br>DGALYGSLHFDPEACSFRELLLEDGYNVYQSEAH<br>GLPLHCPGNKSPHRDPAPRGPCRFLPLPGLPPALPE<br>PPGILAPQPPDVGSSDPLAMVGPSQGRSPSYASEG<br>RGSLLTCGDVEENPGPMRALLARLLLCVLVVSDS<br>KGHGEGTFTSDVSSYLEEQAAKEFIAWLVKGGGG<br>GGGSGGGGSGGGGSAESKYGPPCPSCPAPEFLGGP<br>SVFLFPPKPKDTLMISRTPEVTCVVVDVSQEDPEV<br>QFNWYVDGVEVHNAKTKPREEQFNSTYRVVSVL<br>TVLHQDWLNGKEYKCKVSNKGLPSSIEKTISKAK<br>GQPREPQVYTLPPSQEEMTKNQVSLTCLVKGFYPS<br>DIAVEWESNGQPENNYKTTPPVLDSDGSFAAYSR<br>LTVDKSRWQEGNVFSCSVMHEALHNHYTQKSLS<br>LSPGK |
| 15 | FGF21-GLP1-Fc nucleotide sequence | ATGGACTCGGACGAGACCGGGTTCGAGCACTCA<br>GGACTGTGGGTTTCTGTGCTGGCTGGTCTTCTGC<br>TGGGAGCCTGCCAGGCAGACTCCAGTCCTCTCC<br>TGCAATTCGGGGGCCAAGTCCGGCAGCGGTACC<br>TCTACACAGATGATGCCCAGCAGACAGAAGCCC<br>ACCTGGAGATCAGGGAGGATGGGACGGTGGGG<br>GGCGCTGCTGACCAGAGCCCCGAAAGTCTCCTG<br>CAGCTGAAAGCCTTGAAGCCGGGAGTTATTCAA<br>ATCTTGGGAGTCAAGACATCCAGGTTCCTGTGC<br>CAGCGGCCAGATGGGGCCCTGTATGGATCGCTC<br>CACTTTGACCCTGAGGCCTGCAGCTTCCGGGAG<br>CTGCTTCTTGAGGACGGATACAATGTTTACCAG<br>TCCGAAGCCCACGGCCTCCCGCTGCACTGCCCA<br>GGGAACAAGTCCCCACACCGGGACCCTGCACCC<br>CGAGGACCATGCCGCTTCCTGCCACTACCAGGC<br>CTGCCCCCCGCACTCCCGGAGCCACCCGGAATC<br>CTGGCCCCCCAGCCCCCCGATGTGGGCTCCTCG<br>GACCCTCTGGCCATGGTGGGACCTTCCCAGGGC<br>CGAAGCCCCAGCTACGCTTCCGAGGGCAGAGGA<br>AGTCTGCTAACATGCGGTGACGTCGAGGAGAAT<br>CCTGGACCTATGAGAGCCCTGCTGGCGCGCCTG<br>CTTCTCTGCGTCCTGGTCGTGAGCGACTCCAAA<br>GGCCATGGCGAAGGGACCTTTACCAGTGATGTA<br>AGTTCTTATTTGGAAGAGCAAGCTGCCAAGGAA<br>TTCATTGCTTGGCTGGTGAAAGGCGGCGGAGGC<br>GGAGGCGGAAGCGGAGGCGGAGGAAGCGGCGG<br>TGGCGGCAGCGCTGAGTCCAAATATGGTCCCCC<br>ATGCCCATCATGCCCAGCACCTGAGTTCCTGGG<br>GGGACCATCAGTCTTCCTGTTCCCCCCAAAACC<br>CAAGGACACTCTCATGATCTCCCGGACCCCTGA<br>GGTCACGTGCGTGGTGGTGGACGTGAGCCAGGA<br>AGACCCCGAGGTCCAGTTCAACTGGTACGTGGA<br>TGGCGTGGAGGTGCATAATGCCAAGACAAAGCC<br>GCGGGAGGAGCAGTTCAACAGCACGTACCGTGT<br>GGTCAGCGTCCTCACCGTCCTGCACCAGGACTG<br>GCTGAACGGCAAGGAGTACAAGTGCAAGGTCTC<br>CAACAAGGCCTCCCGTCCTCCATCGAGAAAAC<br>CATCTCCAAAGCCAAAGGGCAGCCCCGAGAGCC<br>ACAGGTGTACACCCTGCCCCCATCCCAGGAGGA<br>GATGACCAAGAACCAGGTCAGCCTGACCTGCCT<br>GGTCAAAGGCTTCTACCCCAGCGACATCGCCGT<br>GGAGTGGGAGAGCAATGGGCAGCCGGAGAACA<br>ACTACAAGACCACGCCTCCCGTGCTGGACTCCG |

TABLE 1-continued description of sequences

| SEQ ID NO | Description | Sequence information |
|---|---|---|
| | | ACGGCTCCTTCGCCGCATACAGCAGGCTAACCG TGGACAAGAGCAGGTGGCAGGAGGGGAATGTC TTCTCATGCTCCGTGATGCATGAGGCTCTGCACA ACCACTACACACAGAAGAGCCTCTCCCTGTCTC CGGGTAAATGA |
| 16 | Primer kspFGF21BamHIF | CGCGGATCCGCCACCATGGACTCGGACGAGACC |
| 17 | Primer IgG4FcSalIR | ACGCGTCGACTCATTTACCCGGAGACAG |
| 18 | Primer SEBP1C-F | CACTGTGACCTCGCAGATCC |
| 19 | Primer SEBP1C-R | ATAGGCAGCTTCTCCGCATC |
| 20 | Primer β-Actin-F | CCTGGCACCCAGCACAAT |
| 21 | Primer β-Actin-R | GGGCCGGACTCGTCATAC |
| 22 | Signal peptide | MRALLARLLLCVLVVSDSKG |

EXAMPLES

The present invention will be described with reference to the following examples which are intended to exemplify the present invention (rather than limit the present invention).

Unless specifically stated otherwise, experiments and methods described in the examples are generally performed according to conventional methods well known in the art and described in various references. If specific conditions are not indicated in the examples, the experiments and methods are conducted in accordance with the conventional conditions or the conditions recommended by the manufacturer. If the reagents or instruments used are not specified with the manufacturers, they are all conventional products that are commercially available. Those skilled in the art know that the examples are provided to exemplify the present invention, rather than limit the protective scope of the present invention. All publications and other references mentioned herein are incorporated herein by reference in their entirety.

Example 1. Preparation of FGF21/GLP1-Fc Modified Mesenchymal Stem Cells 1.1 Isolation and Culture of Autologous Adipose Stem Cells Adipose derived mesenchymal stem cells (AD-MSCs) were isolated through a mixed collagenase digestion method and cultured. The specific method was as follows:

The healthy adult adipose tissue sucked by liposuction was transferred to a 50 mL centrifuge tube, thoroughly washed with PBS, and centrifuged at 1500 rpm for 5 minutes to obtain the upper-layer adipose tissue. Collagenases I, II, and IV were mixed in a ratio of 1:1:1 to prepare 0.2% mixed collagenase, and the adipose tissue was added to the mixed collagenase digestion solution in a ratio of adipose tissue: collagenase=1:1 and placed in a 37° C. shaker to digest for 30 minutes. The digested adipose tissue was immediately added to 10% FBS α-MEM cell culture medium (purchased from Gibco), and centrifuged at 1500 rpm for 10 minutes, such that the cell and tissue aggregates were settled. Then the cells were resuspended in α-MEM complete culture medium, and the undigested tissue was removed through a nylon mesh having a pore size of 100 μm. The cells were inoculated in a culture flask and placed in a 37° C. incubator at saturated humidity and 5% CO2 for static culture. After 2 days, the non-adherent cells were discarded. The flask was gently washed once with PBS, and then complete stem cell culture medium was added. When the cell clones grew to 80% confluence, the cells were digested with 0.05% trypsin and passaged to new culture flasks. P3-generation cells were selected, digested with 0.05% trypsin, washed twice with PBS, and then 5×105 MSCs were labeled with mouse anti-human CD11b-PE, CD45-PE, HLA-DR-PE, CD73-PE, CD90-PE, CD105-PE, CD34-FITC and CD19-FITC antibodies, respectively. The cells were placed at room temperature for 30 minutes in the dark, washed twice with PBS, then fixed with 4% paraformaldehyde, and detected by FACS. The qualified cells were cryopreserved in liquid nitrogen tank, which can be recovered and processed in later use.

1.2 Cloning and Vector Construction of FGF21/GLP1-Fc Genes

A DNA molecule encoding FGF21/GLP1-Fc was obtained via whole gene synthesis from Taihe Biotechnology (Beijing) Co., Ltd., wherein FGF21 (SEQ ID NO: 2, the coding sequence is SEQ ID NO: 3) and GLP1-Fc fusion protein (SEQ ID NO: 10, the coding sequence is SEQ ID NO: 11) were linked by a T2A sequence (SEQ ID NO: 12, the coding sequence is SEQ ID NO: 13). The GLP1-Fc fusion protein, from the N-terminus to the C-terminus, is consisting of GLP1 (SEQ ID NO: 5), linker (SEQ ID NO: 9) and IgG4-Fc (SEQ ID NO: 7), and the N-terminus was further linked with a signal peptide (SEQ ID NO: 22). The DNA molecule encoding FGF21/GLP1-Fc is named as pGSI-seq, and its nucleotide sequence is as shown in SEQ ID NO: 15. The amino acid sequence of FGF21/GLP1-Fc is as shown in SEQ ID NO: 14.

Figure 2:
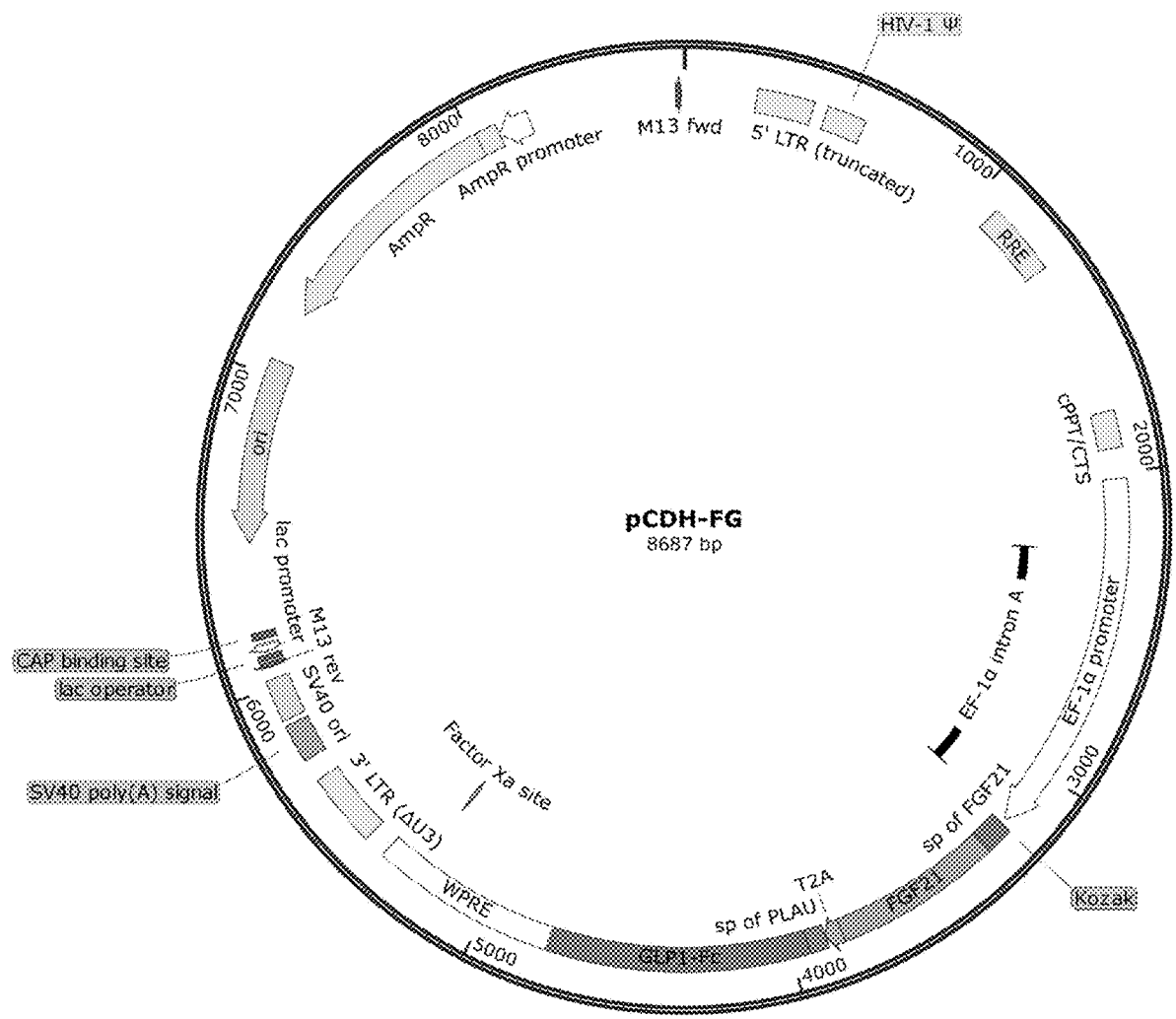
FIG. 2 shows the pCDH-FG plasmid map.

The target fragment kFG (1578 bp) was amplified with 100 ng/μl pGSI-seq as template by using the primer pair kspFGF21BamHIF (5'→3': CGCGGATCCGCCACCATGGACTCGGACGAGACC)+IgG4FcSalIR (5'→3': ACGCGTCGACTCATTTACCCGGAGACAG). The amplified product was analyzed through agarose gel electrophoresis. The results are shown in FIG. 1. BamHI and SalI restriction sites were respectively introduced into the forward and reverse primers. The PCR product was excised from the gel and recovered, then digested with BamHI and SalI. The recombinant lentiviral vector plasmid pCDH-EF1 (purchased from Addgene) was also digested with BamHI and SalI. The digested products were recovered, and then linked with a T4 DNA ligase at 4° C. overnight and transformed to DH5α competent cells. 100 μl of bacterial liquid was taken and plated on LB plates with ampicillin, and the bacteria was cultured at 37° C. overnight. Single clones were picked for colony PCR. Positive clones were sampled for sequencing. The clones with correct sequencing results were preserved, and the plasmid was extracted and named as pCDH-FG. The schematic diagram of the plasmid is shown in FIG. 2.

1.3 Preparation of Lentiviral Vector Carrying FGF21/GLP1-Fc

An aliquot of cryopreserved 293T cells (donated by the Lab217 Embryo Engineering Laboratory of Northeast Agricultural University) was taken from liquid nitrogen and immediately placed in a 37° C. water bath. Then the cells were added dropwise into a 15 ml centrifuge tube containing 5 ml of pre-warmed culture medium, and centrifuged at 1200 rpm for 3 min. The supernatant was discarded. The cells were resuspended in a 293T culture medium (10% FBS+DMEM), inoculated into a 150 mm culture dish, and cultured at 37° C., 5% CO2 and saturated humidity. When the cell confluence reached above 90%, the culture medium was discarded. 5 ml of sterilized PBS solution was added, and the dish was shaken gently to wash the cells. Then the PBS solution was discarded. 2 ml of 0.25% Trypsin-EDTA digestion solution was added to digest for 1-2 minutes until the cells were completely digested. The digestion was terminated by adding a serum-containing culture medium. The cell suspension was centrifuged at 1200 rpm for 3 minutes. Then the cells obtained were resuspended in the culture medium. 1.2×107 cells for packaging lentivirus was inoculated in each 150 mm culture dish, and cultured at 37° C., 5% CO2 and saturated humidity, with 20 ml culture medium/dish.

The 293T cell culture medium was replaced with 18 ml of DMEM culture medium 2 h before transfection. 1 ml of pre-warmed DMEM culture medium was added into sterilized centrifuge tube A. Then the pCDH-FG plasmid, pHelper1 plasmid and pHelper2 plasmid prepared in 1.2 (pCDH-FG:pHelper1:pHelper2=1:1:1, total of 54 μg. The pHelper1 and pHelper2 plasmids were helper plasmids packaged by lentivirus and donated by the Lab217 Embryo Engineering Laboratory of Northeast Agricultural University) were added, and evenly mixed. 1 ml of pre-warmed DMEM culture medium was added into sterilized centrifuge tube B. Then 108 μl of Lipofectamin 2000 (purchased from Invitrogen) solution was added and evenly mixed. Tube A and tube B were incubated for 5 minutes at room temperature. The liquid in the tube B was added dropwise into the tube A, evenly mixed and incubated at room temperature for 20 min, so as to form a DNA-liposome transfection complex.

The DNA-liposome mixture was transferred to 293T cells of which the solution had been replaced beforehand, evenly mixed, and cultured at 37° C., 5% CO2 and saturated humidity. After culturing for 6-8 hours, the culture medium containing the transfection mixture was aspirated and discarded. Cells in each dish were supplemented with 20 ml of pre-warmed DMEM culture medium containing 5% FBS and cultured at 37° C., 5% CO2 and saturated humidity. Then the supernatant was collected respectively at 24 h and 48 h, and temporarily stored at 4° C., and 20 ml fresh culture medium was added. The collected liquid was centrifuged at 4° C. and 3500 rpm for 15 minutes, and the precipitate was discarded. The supernatant was concentrated with a Millipore protein ultrafiltration column (10KD) so as to obtain the lentiviral vector (Lenti-FGF21/GLP1-Fc) carrying FGF21/GLP1-Fc. At the same time, virus titer was measured. The virus was diluted to 1×108 TU/ml according to the virus titer, and then stored at −80° C. after aliquot.

1.4 Genetic Modification of Mesenchymal Stem Cells

The previously cryopreserved P3-generation adipose derived mesenchymal stem cells were recovered in a 150 mm culture dish and cultured in 20 ml serum-free culture medium at 37° C., 5% CO2 and saturated humidity. When the recovered cells became fully confluent, the cells were digested with 0.05% trypsin. The digestion was terminated with a serum-containing culture medium. The cell suspension was centrifuged at 800 rpm for 5 min. The cells obtained by centrifugation were resuspended in an MSC serum-free culture medium (purchased from Bioind).

2-2.5×106 cells were inoculated in each 150 mm culture dish. The cell culture medium was aspirated and discarded the next day after inoculation, and replaced with a serum-free α-MEM culture medium, with 20 ml culture medium/dish. 16 μl of Polybrene (purchased from Sigma) was added. Lenti-FGF21/GLP1-Fc lentivirus (titer 1×108 U/ml) obtained in 1.3 was added at a multiplicity of infection (MOI) of 40, and cultured at 37° C., 5% CO2 and saturated humidity for 6-8 h. After 6-8 hours, the virus-containing α-MEM culture medium was discarded and replaced with a serum-free culture medium. The culture was continued at 37° C., 5% CO2 and saturated humidity for 2-3 days. After the gene-edited cells became fully confluent, the cells were digested with 0.05% trypsin. The digestion was terminated with a serum-containing culture medium. The cell suspension was centrifuged at 800 rpm for 5 min. The cells obtained by centrifuge were resuspended in a serum-free culture medium, passaged in a ratio of 1:6, and cultured in a serum-free culture medium at 37° C. and 5% CO2 for 3 days. The FGF21/GLP1-Fc gene-modified mesenchymal stem cells were named as MSC-FG.

In addition, FGF21 single gene-modified mesenchymal stem cells (MSC-FGF21) and GLP1-Fc single gene-modified mesenchymal stem cells (MSC-GLP1-Fc) were prepared according to the above methods described in 1.1-1.4.

1.5 Verification of MSC-FG Biological Functions

Figure 3:
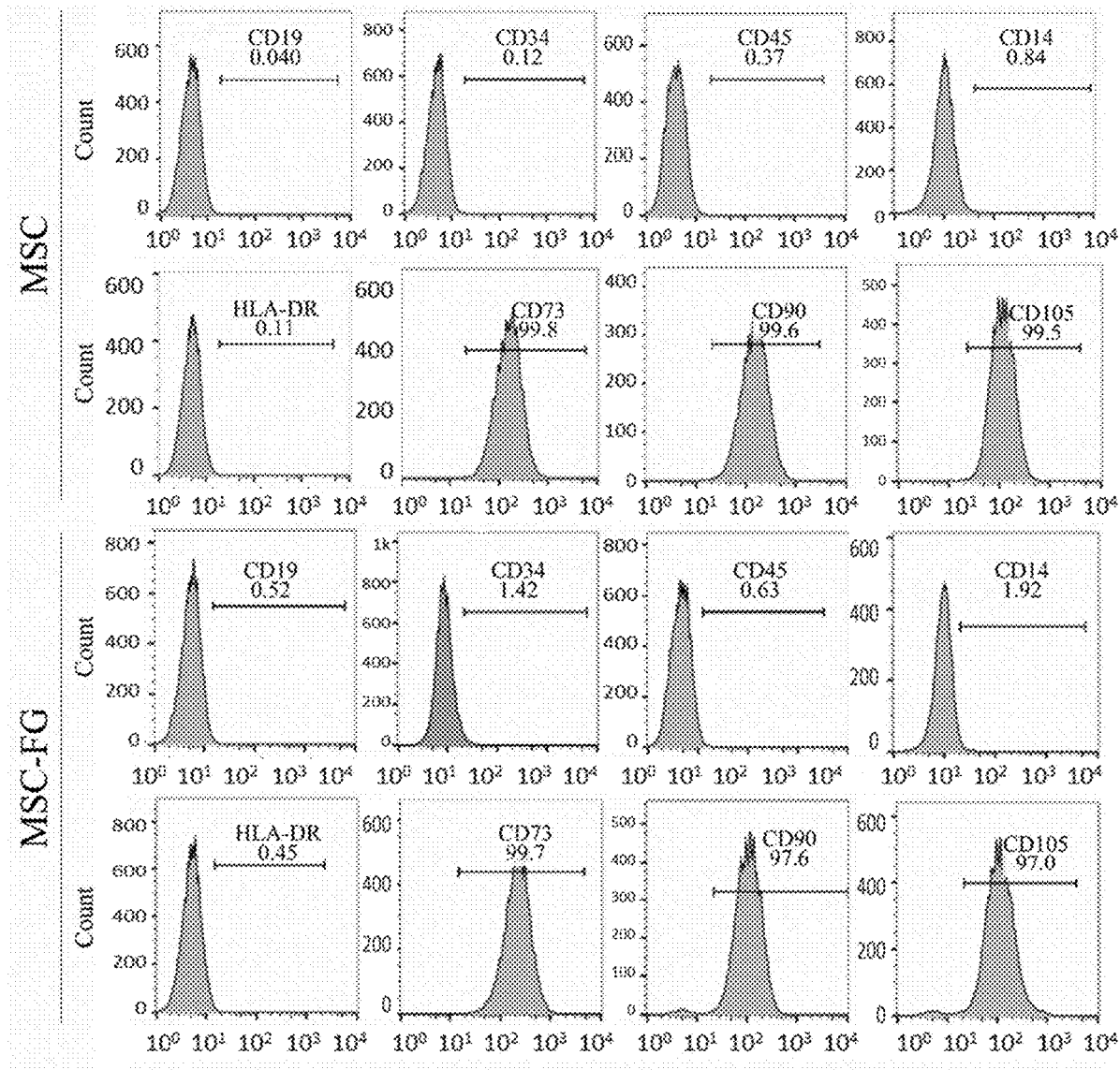
FIG. 3 shows the flow cytometry diagram of MSC and MSC-FG cell surface markers.

Cell phenotype identification: MSCs and MSC-FGs of P6 generation were selected, digested with 0.05% trypsin and washed twice with PBS, and then MSCs were labeled with mouse anti-human CD14-PerCp-Cy5.5, CD19-PE, CD34-PE, CD45-PE or CD45-FITC, HLA-DR-PE, CD73-PE, CD90-PE and CD105-PE (Becton, Dickinson and Company) antibodies. Each sample contained about 1×106 cells were contained for detection. The cells were incubated at room temperature in the dark for 30 min, washed twice with PBS, then immobilized with 2% paraformaldehyde and detected with a flow cytometer. The results are shown in FIG. 3. The results showed after Lenti-FGF21/GLP1-Fc lentivirus infection, the characteristics of the MSC cells still retained based on the cell surface marker, i.e. CD73, CD90 and CD105 were positive (>90%), and CD14, CD19, CD34, CD45 and HLA-DR were negative (<1%).

Figure 4:
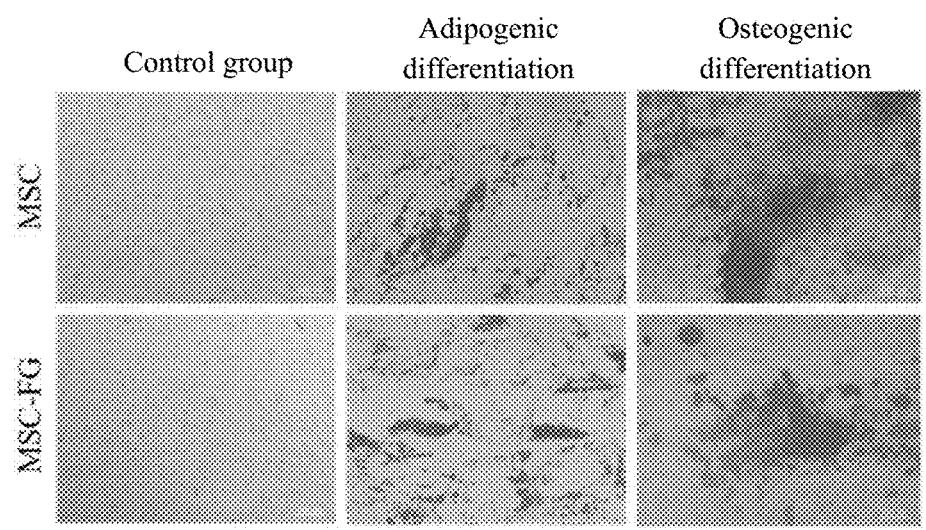
FIG. 4 shows the staining of MSC and MSC-FG cells for adipogenesis and osteogenic differentiation.

Guided differentiation induction (adipogenic and osteogenic induction): MSCs and MSC-FGs of P6 generation were collected, digested with 0.05% trypsin, and plated in a 12-well plate at a cell density of 2×105 cells/well. The culture medium was replaced with adipogenic induction culture medium and osteogenic induction culture medium (purchased from BI company) on the second day. Then the culture medium was replaced every 2 days. Oil Red O staining was performed after 18 days of adipogenic induction, and Alizarin Red-S staining was performed after 23 days of osteogenic induction. The results are shown in FIG. 4. The results showed that MSC cells (MSC-FG) infected by Lenti-FGF21-GLP1-Fc lentivirus still had capabilities of adipogenic and osteogenic differentiation.

Figure 5:
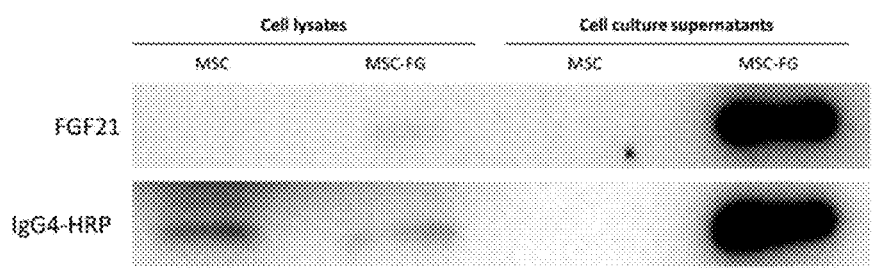
FIG. 5 shows the FGF21 and GLP1-Fc expression levels in MSC and MSC-FG cells and cell supernatants by western blot.

FGF21 and GLP1-Fc expression: MSC and MSC-FG cell lysates as well as cell culture supernatants of MSC and MSC-FG after 10× concentration were collected and subjected to 15% SDS-PAGE gel electrophoresis and wet-transferred to PVDF membranes. The membranes were then blocked with 5% skim milk. Antibody FGF21 (1:3000, Abcam, for detecting FGF21 protein expression) and antibody IgG4-HRP (1:3000, Abcam, for detecting GLP1-Fc protein expression) were added and incubated with the membranes overnight at 4° C. Then the membranes were washed three times with TBST and further incubated with secondary antibody for 1 h, followed by washing of three times with TBST. Then color was developed with a chemiluminescence kit, and the exposure was conducted with a computer image analysis system. The results are shown in FIG. 5. The results showed that, in FGF21/GLP1-Fc double gene-modified MSC cell (MSC-FG) supernatant comprises high levels of FGF21 and GLP1-Fc, but fewer levels were detected within the cells.

Example 2. Evaluation of Biological Activity of FGF21/GLP1-Fc Modified Mesenchymal Stem Cells In Vitro 2.1 Effect of MSC-FG on Glucose-Stimulated Insulin Secretion Preparation: MSC, MSC-FG, MSC-FGF21 and MSC-GLP1-Fc cells obtained in Example 1 were cultured in 100 mm culture dish, respectively. When the cell confluence reached 70%-80%, the original MSC serum-free culture medium was aspirated and discarded, and the cells were further cultured with 10 ml of α-MEM culture medium at 37° C., 5% CO2 and saturated humidity for 48 hours. The culture supernatants of four types of cells were collected, concentrated for 10× with an ultrafiltration column, and stored at 4° C. for later use. For long-term storage, the supernatants needed to be placed in a −80° C. refrigerator.

An aliquot of cryopreserved INS-1 cells (rat insulinoma cells, donated by the Academy of Military Medical Sciences) from liquid nitrogen was quickly placed in a 37° C. water bath, then the cells were added dropwise into a 15 ml centrifuge tube containing 5 ml of pre-warmed culture medium, and centrifuged at 1200 rpm for 3 min. The supernatant was discarded. The cells were resuspended in INS-1 culture medium (10% FBS+1 mM sodium pyruvate+2 mM glutamine+50 µM mercaptoethanol+1640 culture medium), inoculated into a 100 mm culture dish, and cultured at 37° C., 5% CO2 and saturated humidity. Then the cells were regularly passaged every 2-3 days with a ratio of 1:3. After the cells became fully confluent, the culture medium was discarded. 2 ml sterilized PBS solution was added and shaken gently to wash the cells. Then the PBS solution was discarded. 2 ml of 0.25% Trypsin-EDTA digestion solution was added to digest for 2-3 minutes until the cells were completely digested. The digestion was terminated by adding a serum-containing culture medium. The cell suspension was centrifuged at 1200 rpm for 3 min. The cells obtained by centrifuge were resuspended in the culture medium. Each well of a 6-well plate was inoculated with $1 \times 10^6$ cells. Then 2 ml of INS-1 culture medium was added to the well, and the cells were cultured at 37° C., 5% CO2 and saturated humidity. When the cell density reached 70%-80%, the cells were used for functional verification.

The original INS-1 culture medium in the 6-well plate was aspirated and discarded. 2 ml of pre-warmed low-glucose KRBH buffer (129 mM NaCl+4.8 mM KCl+1.2 mM KH2PO4+1.2 mM MgSO4+2 mM CaCl2+20 mM HEPES+24 mM NaHCO3+0.2% BSA+0.4 mg/ml glucose) was added to starve the INS-1 cells for two hours. The low-glucose KRBH buffer was aspirated and discarded. 2 ml of pre-warmed high-glucose KRBH buffer (129 mM NaCl+ 4.8 mM KCl+1.2 mM KH2PO4+1.2 mM MgSO4+2 mM CaCl2+20 mM HEPES+24 mM NaHCO3+0.2% BSA+3 mg/ml glucose) was added. Then the cells were supplemented with 500 µl of previously collected and concentrated culture supernatants of MSC, MSC-FGF21, MSC-GLP1-Fc and MSC-FG, respectively, and cultured at 37° C., 5% CO2 and saturated humidity for 2 hours.

Figure 6:
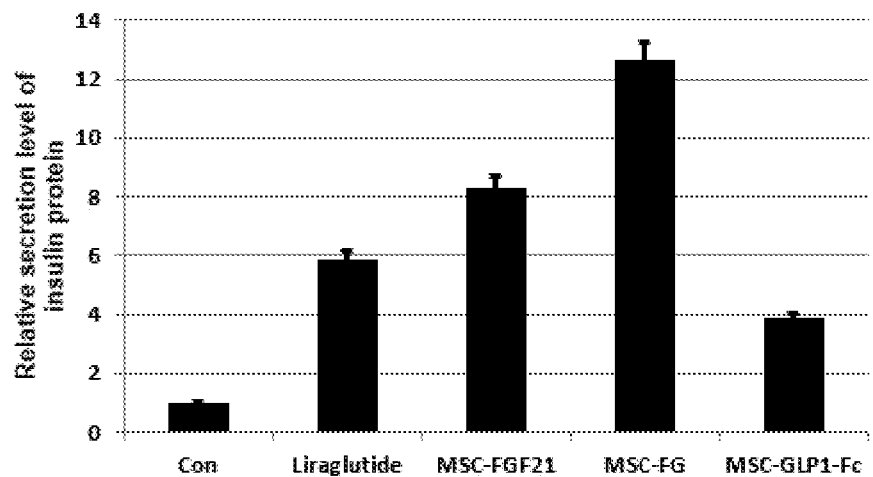
FIG. 6 shows the effects of MSC-FGF21, MSC-GLP1-Fc and MSC-FG culture supernatants on insulin secretion level of INS-1 cells after glucose stimulation.

Then supernatants were collected, and the insulin content therein was detected by radioimmunoassay. The results are shown in FIG. 6. The results showed that the culture supernatant of FGF21/GLP1-Fc double gene-modified MSC cells (MSC-FG) could stimulate INS-1 to secrete and express insulin, and the level was significantly higher than that of the FGF21 single gene-modified MSC (MSC-FGF21) culture supernatant and that of the GLP1-Fc single gene-modified MSC (MSC-GLP1-Fc) culture supernatant. Thus, it can be seen that the FGF21/GLP1-Fc double gene-modified MSC cells significant synergistic effect in regulating insulin secretion.

2.2 Effect of MSC-FG on the Expression Level of Sterol Metabolism Gene SREBP1c

Preparation: MSC, MSC-FG, MSC-FGF21 and MSC-GLP1-Fc cells obtained in Example 1 were cultured in 100 mm culture dish, respectively. When the cell confluence reached 70%-80%, the original MSC serum-free culture medium was aspirated and discarded, and the cells were further cultured with 10 ml of α-MEM culture medium at 37° C., 5% CO2 and saturated humidity for 48 hours. The culture supernatants of four types of cells were collected and stored at 4° C. for later use. For long-term storage, the supernatants needed to be placed in a −80° C. refrigerator.

An aliquot of cryopreserved HePG2 cells (human liver cancer cells, donated by the Academy of Military Medical Sciences) from liquid nitrogen was quickly placed in a 37° C. water bath, then the cells were added dropwise into a 15 ml centrifuge tube containing 5 ml of pre-warmed culture medium, and centrifuged at 1200 rpm for 3 min. The supernatant was discarded. The cells were resuspended in HePG2 culture medium (10% FBS+DMEM), inoculated into a 100 mm culture dish, and cultured at 37° C., 5% $CO_2$ and saturated humidity. Then the cells were regularly passaged every 2-3 days with a ratio of 1:6. After the cells became fully confluent, the culture medium was discarded. 2 ml sterilized PBS solution was added and shaken gently to wash the cells. Then the PBS solution was discarded. 2 ml of 0.25% Trypsin-EDTA digestion solution was added to digest for 2-3 minutes until the cells were completely digested. The digestion was terminated by adding a serum-containing culture medium. The cell suspension was centrifuged at 1200 rpm for 3 min. The cells obtained by centrifuge were resuspended in the culture medium. Each well of a 6-well plate was inoculated with $1 \times 10^6$-$2 \times 10^6$ cells. Then 2 ml of culture medium was added to the well, and the cells were cultured at 37° C., 5% $CO_2$ and saturated humidity. When the cell density reached 70%-80%, the cells were used for functional verification.

The original HePG2 culture medium in the 6-well plate was aspirated and discarded. 2 ml of previously collected MSC, MSC-FGF21, MSC-GLP1-Fc and MSC-FG culture supernatants were added. The cells were cultured at 37° C., 5% $CO_2$ and saturated humidity for 24 hours followed by digestion. After centrifuge, the cells were collected for RNA extraction via TRIzol. Then the RNA concentration was measured, and 500 ng of total RNA was reverse transcribed into cDNA using a reverse transcription kit (All-in-One cDNA Synthesis SuperMix).

Figure 7:
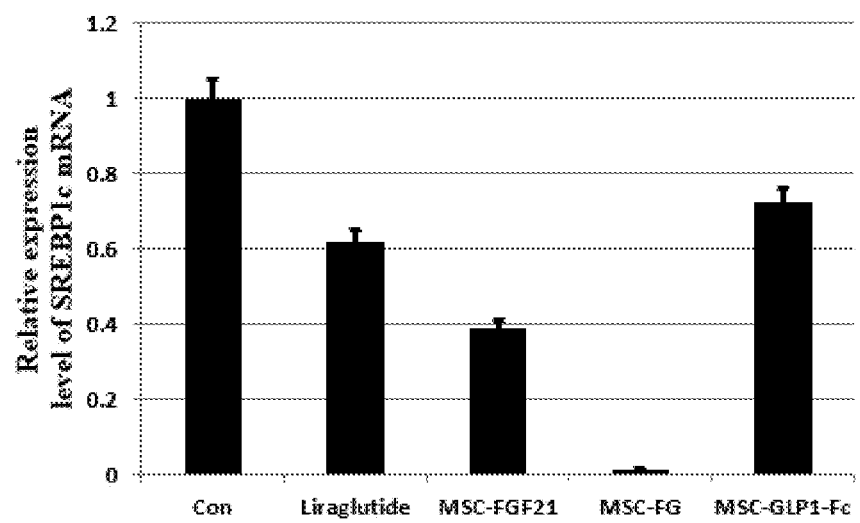
FIG. 7 shows the effects of MSC-FGF21, MSC-GLP1-Fc and MSC-FG culture supernatants on mRNA expression level of sterol metabolic gene SREBP1C.

RT-qPCR detection was performed according to the instructions of Takara's Fluorescence Real-Time Quantification Kit (SYBR® Premix Ex Taq™). Primer sequence (5'→3'): SEBP1C-F: CACTGTGACCTCGCAGATCC; SEBP1C-R: ATAGGCAGCTTCTCCGCATC; β-Actin-F: CCTGGCACCCAGCACAAT; β-Actin-R: GGGCCGGACTCGTCATAC The results are shown in FIG. 7. The culture supernatant of the FGF21/GLP1-Fc double gene-modified MSC cells (MSC-FG) could significantly inhibit the mRNA expression level of SREBP1c (hepatic tissue sterol regulatory element binding protein-1C), and the inhibition activity was significantly higher than that of the culture supernatants of MSC-FGF21 and MSC-GLP1-Fc. Thus, it can be seen that the FGF21/GLP1-Fc double gene-modified MSC cells present significant synergistic effect in regulating lipid metabolism.

Example 3. Evaluation of Biological Activity of FGF21/GLP1-Fc Modified Mesenchymal Stem Cells In Vivo 3.1 Experimental Grouping Thirty 5-week-old male diabetic model mice BKS.Cg-Dock7m+/+Leprdb/Nju (purchased from the Model Animal Research Center of Nanjing University) were divided into control group (physiological saline), liraglutide group (drug), MSC group (cell), MSC-FGF21 group (cell), MSC-FG group (cell) and MSC-GLP1-Fc group (cell), a total of 6 groups (5 mice in each group).

3.2 Therapeutic Regimen

The drug was injected subcutaneously for the liraglutide group (Liraglutide), and the control and the cells were injected intraperitoneally for the remaining groups. The drugs were administrated in the morning for all groups.

Administration frequency: For the cell groups, the cells were injected every 7 days for a total of 3 times. For the liraglutide group, the drug was administered twice a week.

Administration dosage for each group:

Control group (physiological saline group): each mouse was injected intraperitoneally with 100 μl of physiological saline each time.

Cell groups: each mouse was intraperitoneally injected every 7 days at a dose of 1×106 cells/100 μl.

Liraglutide group: the drug was subcutaneously injected every 3-4 days with an effective concentration of 0.5 mg/Kg.

3.3 Detection Index

Measurement of fasting blood glucose and fasting body weight: the mice were starved on the night of cell injection (fasting, normal water supply) for 12 hours. Blood glucose and body weight were measured in the next morning. The body weight change curve was drawn according to the average blood glucose and body weight of the mice.

Detection of serum biochemical indexes: after 28 days of treatment, blood was collected from the eyeballs of the mice. The blood was centrifuged at 3000 rpm for 10 minutes to separate serum. The samples were sent to Beijing Beifangshengke Medical Technology Co., Ltd. for detection of triglyceride (TG), total cholesterol (TG), high-density lipoprotein (HDL), low-density lipoprotein (LDL) and insulin (INS) indexes.

Hematoxylin-eosin (HE) staining of animal tissues: after 28 days of treatment, the mice were sacrificed by neck breaking. A median abdominal incision was performed to fully expose the abdomen to collect liver and abdominal subcutaneous fat of the mice. The tissues were immobilized by 10× volume of 4% polymerized formaldehyde for 24 hours, and then subjected to paraffin-embedment and hematoxylin-eosin (HE) staining.

3.4 Experimental Results

Figure 8:
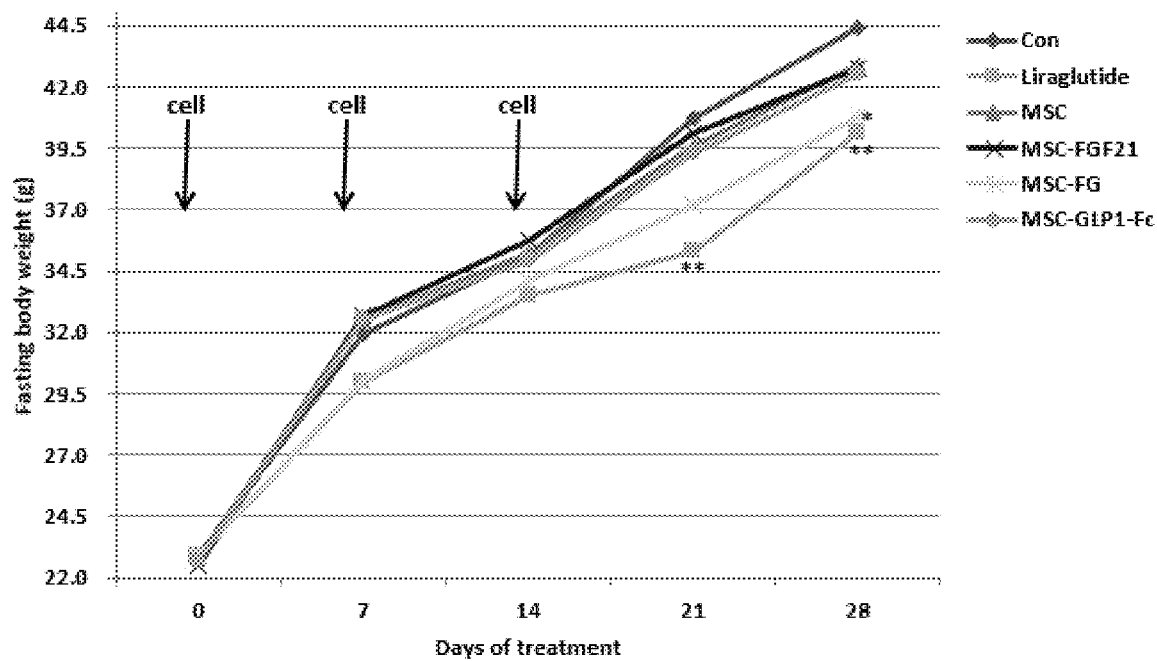
FIG. 8 shows the body weight of fasting diabetic model mice. Liraglutide is the positive control group. The arrows represent the time points of administering drugs and cells. * represents significant different compared to Con group, and ** represents extremely significant different compared to Con group.
Figure 9:
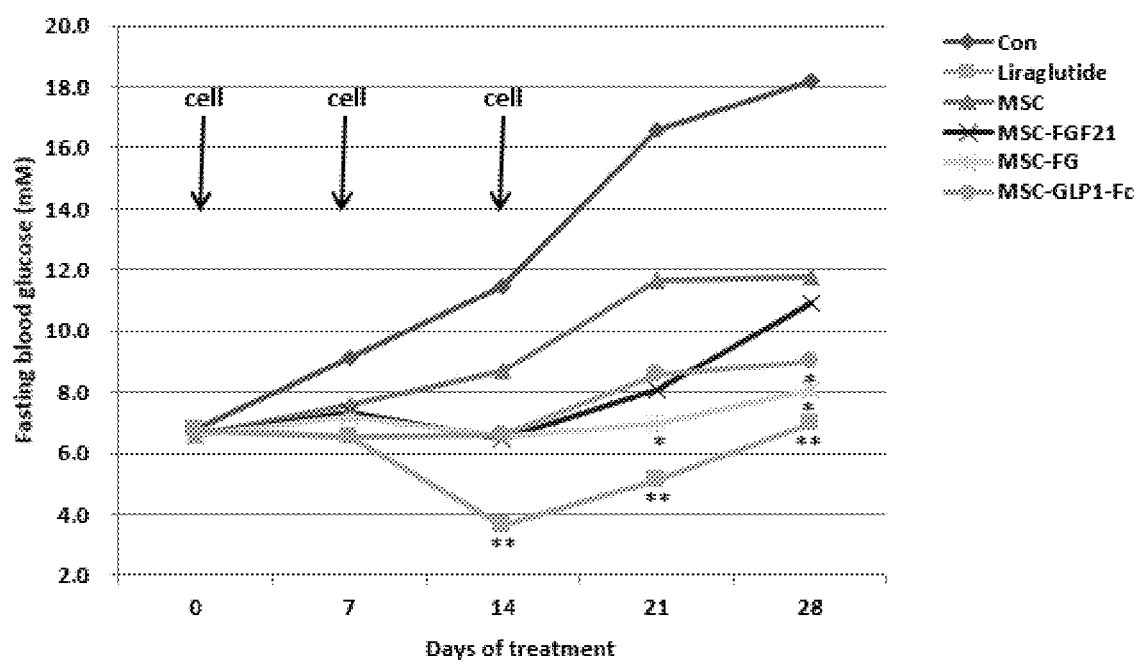
FIG. 9 shows the blood glucose of fasting diabetic model mice. Liraglutide is the positive control group. The arrows represent the time points of administering drugs and cells. * represents significant different compared to Con group, and ** represents extremely significant different compared to Con group.

BKS diabetic mice were administrated with 3 times of cell therapies, and fasting blood glucose and body weight of the mice were measured once a week since the first treatment. After the treatment, the mice were subject to observation for two more weeks. The average body weight and blood glucose change curves of the mice are shown in FIG. 8 and FIG. 9, respectively. The results showed that after 28 days of treatment, the mice in the MSC-FG cell therapy group had significantly reduced body weight compared to the mice in the control group (*P<0.05), and the values were similar to those of the positive control Liraglutide, and significantly better than those of the MSC-FGF21 and MSC-GLP1-Fc groups (FIG. 8). Meanwhile, the mice in the MSC-FG cell therapy group had significantly different fasting blood glucose compared to the mice in the control group (*P<0.01). Moreover, the effect of treatment was displayed in the third cell therapy, and the trend was the same as that of the positive control Liraglutide and significantly better than that of the MSC-FGF21 and MSC-GLP1-Fc groups (FIG. 9).

Figure 10:
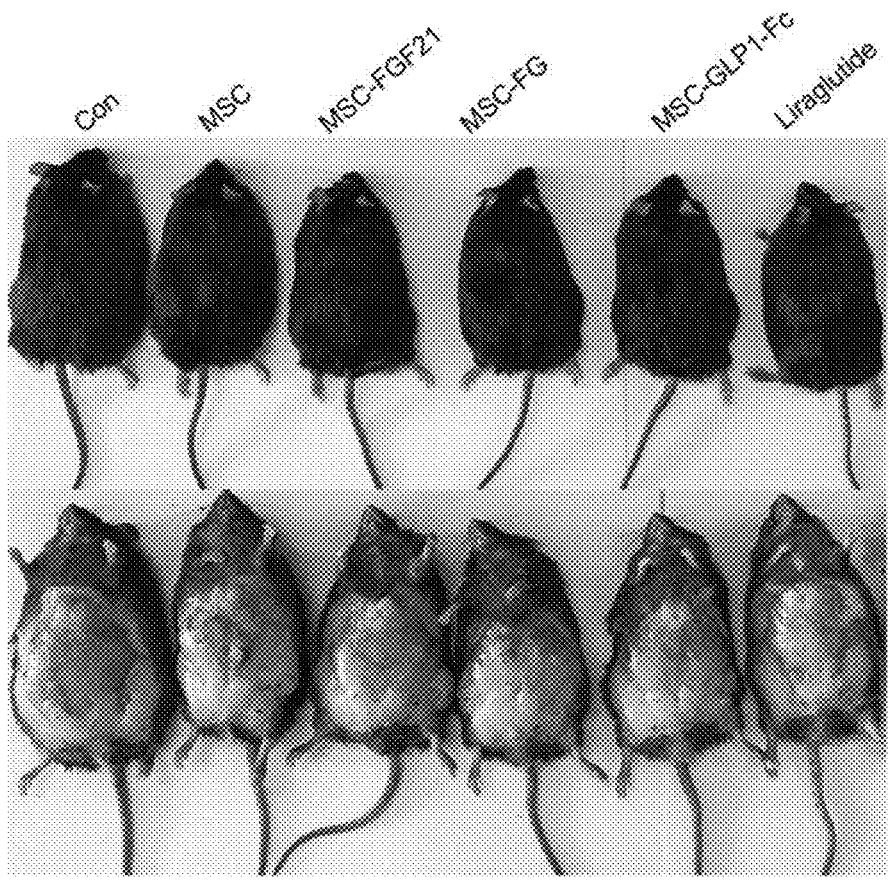
FIG. 10 shows the body sizes of diabetic model mice in different experimental groups after 28 days of cell therapy. Liraglutide is the positive control group.
Figure 11:
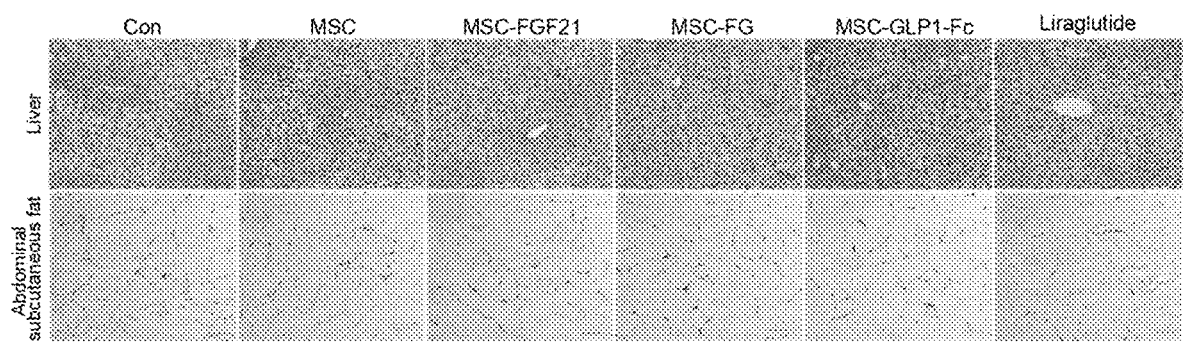
FIG. 11 shows HE staining of liver and abdominal subcutaneous fat of diabetic model mice in different experimental groups after 28 days of cell therapy. Liraglutide is the positive control group.

After 28 days of treatment, the body size of the mice in the MSC-FG cell therapy group was also significantly smaller than that of the control mice, and the content of the abdominal subcutaneous fat was significantly reduced (FIG. 10). HE staining of liver tissue sections (FIG. 11) showed that the liver of Con mice showed severe steatosis. The liver tissue was filled with adipocytes, and massive amounts of hepatocytes were necrotic. After treatment with MSC-FG cells, the liver steatosis was significantly improved, and the degree of fibrosis was declined. HE staining of the abdominal subcutaneous fat (FIG. 11) showed that the adipocytes of the Con mice were excessively enlarged and the cell nuclei were irregular. After treatment with MSC-FG, the volume of the adipocytes was significantly reduced.

Figure 12:
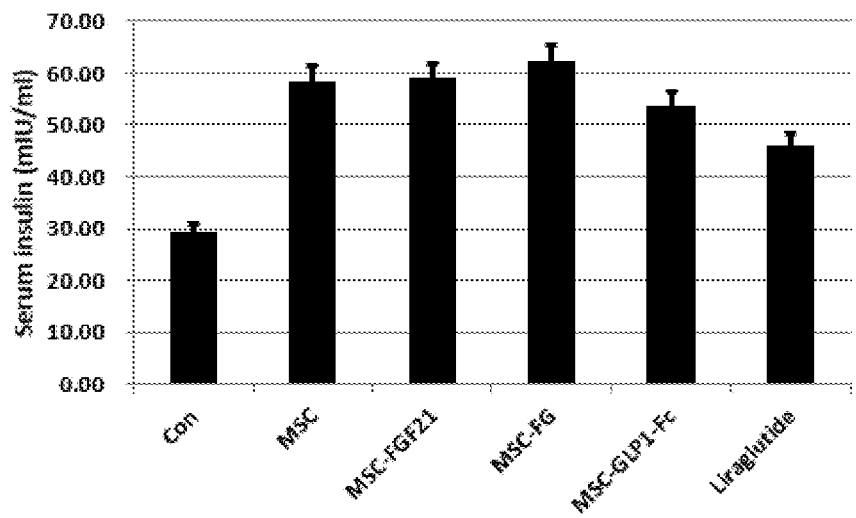
FIG. 12 shows the serum insulin levels of diabetic model mice in different experimental groups after 28 days of cell therapy. Liraglutide is the positive control group.
Figure 13:
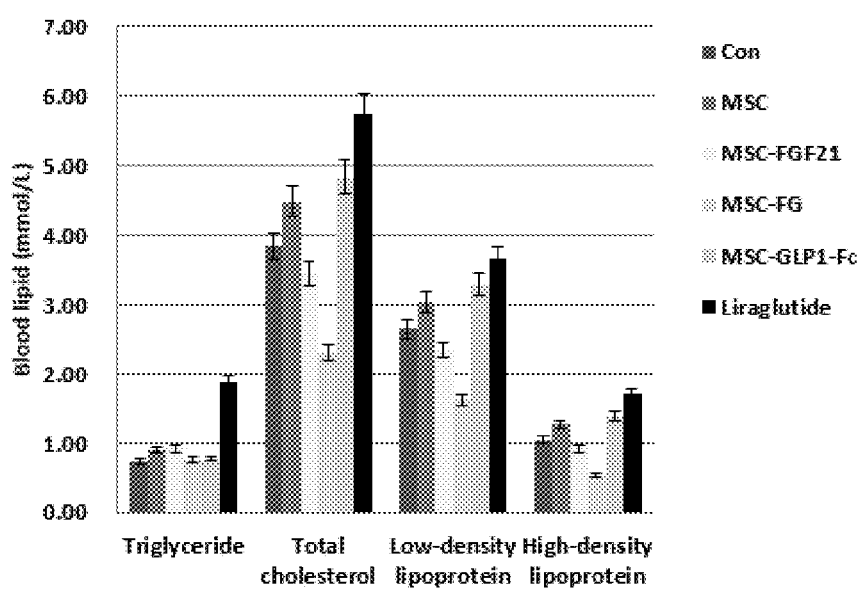
FIG. 13 shows the serum blood lipid levels of diabetic model mice detected in different experimental groups after 28 days of cell therapy. Liraglutide is the positive control group.

Following 28 days of treatment, the serum biochemical test of the mice revealed that, the serum insulin level of the mice treated with MSC-FG was increased significantly after feeding, which was even significantly better than that of the mice treated with the positive control Liraglutide (FIG. 12). After treatment with MSC-FG, TC (total cholesterol), LDL (low-density lipoprotein) and HDL (high-density lipoprotein) and other indexes in the serum of the mice decreased significantly, which were better than those of the MSC-FGF21 and MSC-GLP1-Fc groups (FIG. 13).

It can be seen that MSC-FGF1 can significantly reduce the body weight and blood glucose of the mice, and also can reduce the blood lipid level, relieve the occurrence of fatty liver, improve abnormal lipid metabolism and repair islet cell function. Moreover, MSC-FGF1 showed better therapeutic efficacy than the MSC-FGF21 and MSC-GLP1-Fc groups, displayed a significant synergistic effect, and was also significantly superior than the hypoglycemic drug Liraglutide in improving blood lipids. Therefore, the modified MSC of the present invention is particularly suitable for treating metabolic diseases.

Although the embodiments of the present invention have been described in detail, those skilled in the art will understand that various modifications and changes can be made to the details according to all teachings that have been published, and these changes are all included within the protective scope of the present invention. The entire of the present invention is given by appended claims and any equivalents thereof.

What is claimed is:

1. A method of treating diabetes in a subject in need thereof, the method comprising administering to the subject:
   (i) a mesenchymal stem cell that expresses:
      (a) a first protein comprising an amino acid sequence that has at least 97.0% sequence identity to the sequence set forth in SEQ ID NO: 2, wherein the first protein exhibits fibroblast growth factor 21 (FGF21) activity, and
      (b) a second protein comprising an amino acid sequence that has at least 80% sequence identity to the sequence set forth in SEQ ID NO: 5, wherein the second protein exhibits glucagon-like polypeptide 1 (GLP1) activity; or
   (ii) a composition comprising the mesenchymal stem cell and a culture medium.

2. The method of claim 1, wherein the first protein or the second protein is a fusion protein that further comprises an additional polypeptide.

3. The method of claim 2, wherein the additional polypeptide is configured to extend a half-life of the fusion protein in vivo.

4. The method of claim 2, wherein the additional polypeptide is selected from an immunoglobulin Fc domain, a serum albumin, an albumin binding polypeptide, a transferrin, and a functional fragment thereof.

5. The method of claim 2, wherein the additional polypeptide comprises an Fc domain of human IgG1, IgG2, IgG3, or IgG4.

6. The method of claim 2, wherein the additional polypeptide comprises the amino acid sequence set forth in SEQ ID NO: 7.

7. The method of claim 1, wherein the mesenchymal stem cell is configured to secrete the first protein and the second protein.

8. The method of claim 1, wherein the method ameliorates one or more symptoms of type II diabetes in the subject.

9. The method of claim 1, wherein the mesenchymal stem cell is configured to promote secretion of insulin at a higher level by an insulin-expressing cell in response to a glucose challenge as compared to a corresponding cell that expresses the first protein or the second protein alone.

10. The method of claim 1, wherein the second protein comprises an amino acid sequence that has at least 90% sequence identity to the sequence set forth in SEQ ID NO: 10.

11. The method of claim 1, wherein the second protein comprises an amino acid sequence that has at least 91% sequence identity to the sequence set forth in SEQ ID NO: 5.

12. The method of claim 1, wherein the first protein comprises an amino acid sequence that has at least 98% sequence identity to the sequence set forth in SEQ ID NO: 2.

13. The method of claim 1, wherein the first protein comprises an amino acid sequence that has 100% sequence identity to the sequence set forth in SEQ ID NO: 2.

14. The method of claim 1, wherein the second protein comprises an amino acid sequence that has at least 95% sequence identity to the sequence set forth in SEQ ID NO: 5.

15. The method of claim 1, wherein the second protein comprises an amino acid sequence that has 100% sequence identity to the sequence set forth in SEQ ID NO: 5.

16. The method of claim 1, wherein the mesenchymal stem cell hosts a first exogenous nucleic acid sequence and a second exogenous nucleic acid sequence, and wherein the first exogenous nucleic acid sequence encodes the first protein and the second exogenous nucleic acid sequence encodes the second protein.

17. The method of claim 16, wherein the first exogenous nucleic acid sequence and the second exogenous nucleic acid sequence are integrated in the genome of the mesenchymal stem cell.

18. The method of claim 16, wherein the first exogenous nucleic acid sequence and the second exogenous nucleic acid sequence are linked by a nucleic acid sequence encoding a self-cleaving peptide.

19. The method of 18, wherein the self-cleaving peptide is a 2A peptide.

* * * * *